(12) United States Patent
Farhadi

(10) Patent No.: US 11,925,319 B2
(45) Date of Patent: Mar. 12, 2024

(54) ENDOSCOPIC ACCESSORY

(71) Applicant: IzoMed, Inc., Irvine, CA (US)

(72) Inventor: Ashkan Farhadi, Irvine, CA (US)

(73) Assignee: IzoMed, Inc, Irvine, CA (US)

( * ) Notice: Subject to any disclaimer, the term of this patent is extended or adjusted under 35 U.S.C. 154(b) by 0 days.

(21) Appl. No.: 18/310,228

(22) Filed: May 1, 2023

(65) Prior Publication Data

US 2023/0301496 A1   Sep. 28, 2023

Related U.S. Application Data

(63) Continuation of application No. PCT/US2023/016637, filed on Mar. 28, 2023, which is a continuation-in-part of application No. 18/149,448, filed on Jan. 3, 2023, which is a continuation of application No. 17/806,920, filed on Jun. 14, 2022, now Pat. No. 11,553,830, and a continuation-in-part of application No. 63/362,020, filed on Mar. 28, 2022.

(51) Int. Cl.
*A61B 1/00* (2006.01)
*A61B 1/015* (2006.01)
*A61B 1/018* (2006.01)
*A61B 1/31* (2006.01)

(52) U.S. Cl.
CPC ...... *A61B 1/00135* (2013.01); *A61B 1/00082* (2013.01); *A61B 1/015* (2013.01); *A61B 1/018* (2013.01); *A61B 1/31* (2013.01)

(58) Field of Classification Search
CPC ... A61B 1/00135; A61B 1/0082; A61B 1/015; A61B 1/018; A61B 1/31; A61B 1/0014
USPC .................................................. 600/104, 114
See application file for complete search history.

(56) References Cited

U.S. PATENT DOCUMENTS

| | | |
|---|---|---|
| 3,726,283 A | 4/1973 | Dye et al. |
| 4,362,150 A | 12/1982 | Lombardi |
| 4,809,678 A | 3/1989 | Klein et al. |
| 5,210,814 A | 5/1993 | Mcnally |
| 5,217,001 A | 6/1993 | Nakao et al. |
| 5,441,503 A | 8/1995 | Considine |
| 5,660,175 A | 8/1997 | Dayal |
| 5,762,604 A | 6/1998 | Kieturakis et al. |
| 5,779,624 A | 7/1998 | Chang |
| 5,827,304 A | 10/1998 | Hart |
| 5,836,907 A | 11/1998 | Campbell |
| 5,904,648 A | 5/1999 | Arndt |
| 5,916,145 A | 6/1999 | Chu |
| 6,234,958 B1 | 5/2001 | Snoke et al. |

(Continued)

FOREIGN PATENT DOCUMENTS

| WO | WO 2007/017854 | 2/2007 |
|---|---|---|
| WO | WO 2021/242884 | 12/2021 |
| WO | WO 2023/192330 | 10/2023 |

*Primary Examiner* — John P Leubecker
*Assistant Examiner* — Li-Ting Song
(74) *Attorney, Agent, or Firm* — Levine Bagade Han LLP

(57) ABSTRACT

Devices and methods of use for an endoscopic accessory device that can be assembled and advanced over an endoscope positioned at a site within the body, the endoscopic accessory device including a body structure having seam structures on opposite sides of an elongate body structure, where the seam structures can be releasably joined to transform the body structure from a planar configuration to a tubular configuration.

19 Claims, 20 Drawing Sheets

(56) References Cited

U.S. PATENT DOCUMENTS

| | | |
|---|---|---|
| 6,440,061 B1 | 8/2002 | Wenner et al. |
| 6,569,085 B2 | 5/2003 | Kortenbach et al. |
| 6,585,639 B1 | 7/2003 | Kotmel et al. |
| 7,052,456 B2 | 5/2006 | Simon |
| 8,225,794 B2 | 7/2012 | Mikkaichi et al. |
| 9,480,390 B2 | 11/2016 | Farhadi |
| 10,149,601 B2 | 12/2018 | Cornhill |
| 11,076,743 B2 | 8/2021 | Cornhill |
| 11,553,830 B1 | 1/2023 | Farhadi |
| 2001/0049509 A1 | 12/2001 | Sekine et al. |
| 2002/0077527 A1 | 6/2002 | Aydelotte et al. |
| 2002/0185135 A1 | 12/2002 | Amar |
| 2004/0210110 A1 | 10/2004 | Nakao |
| 2004/0221853 A1 | 11/2004 | Miller |
| 2005/0107664 A1 | 5/2005 | Kalloo |
| 2006/0020165 A1 | 1/2006 | Adams |
| 2006/0074274 A1 | 4/2006 | Friedman |
| 2006/0161044 A1 | 7/2006 | Oneda et al. |
| 2007/0015965 A1* | 1/2007 | Cox ............... A61B 1/00078 600/116 |
| 2007/0112250 A1 | 5/2007 | Kura |
| 2008/0171989 A1 | 7/2008 | Bell |
| 2009/0227835 A1 | 9/2009 | Terliuc |
| 2011/0105840 A1 | 5/2011 | Terliuc et al. |
| 2011/0251458 A1 | 10/2011 | Terliuc et al. |
| 2012/0022574 A1 | 1/2012 | Mafi |
| 2013/0012772 A1* | 1/2013 | Gunday ........... A61B 17/22012 600/104 |
| 2013/0281781 A1 | 10/2013 | Farhadi |
| 2014/0316265 A1* | 10/2014 | Levin ................. A61B 6/037 600/114 |
| 2015/0094611 A1 | 4/2015 | Farhadi |
| 2015/0105621 A1* | 4/2015 | Farhadi ............ A61B 1/00135 600/115 |
| 2016/0081537 A1 | 3/2016 | Farhadi |
| 2017/0027415 A1 | 2/2017 | Terliuc et al. |
| 2019/0335982 A1 | 11/2019 | Johann |
| 2020/0000683 A1 | 1/2020 | Wolkenstoerfer et al. |
| 2020/0121168 A1 | 4/2020 | Milsom et al. |
| 2020/0146530 A1 | 5/2020 | Cruz |
| 2020/0245848 A1 | 8/2020 | Johann |
| 2021/0338056 A1 | 11/2021 | Nakajima |
| 2021/0338920 A1 | 11/2021 | Nakajima |
| 2021/0361272 A1 | 11/2021 | Nakajima |
| 2022/0183540 A1 | 6/2022 | Johann et al. |

* cited by examiner

ENDOSCOPIC ACCESSORY

CROSS-REFERENCE TO RELATED APPLICATIONS

This application is a continuation of PCT/US2023/016637 filed Mar. 28, 2023, which is a continuation-in-part of U.S. patent application Ser. No. 18/149,448 filed Jan. 3, 2023, which is a continuation of U.S. patent application Ser. No. 17/806,920 filed Jun. 14, 2022, now U.S. Pat. No. 11,553,830. This application is also a continuation in part of U.S. Provisional application No. 63/362,020 filed Mar. 28, 2022. The entirety of all of the above are incorporated by reference.

FIELD OF INVENTION

The devices described herein relate to an accessory device for improving examination of body organs, particularly a gastrointestinal tract.

BACKGROUND OF INVENTION

Endoscopy is a well-known procedure for examining the internal organs. The procedure is performed under the guidance of an endoscope. Currently used fiber optic endoscopes include lenses mounted in a flexible tube that relay an image from inside a body cavity for viewing by a physician for diagnosis or manipulation inside the body cavity.

In performing an endoscopy, it is common to insufflate (introduce air into) the gastrointestinal tract in order to provide easier visualization. This can cause bloating and discomfort to the patient or, in rare cases, severe abdominal pain.

Since the gastrointestinal tract is a hollow organ, it is not possible to keep the insufflation limited to part of gastrointestinal tract that needs to be examined. Accordingly, there remains a need for an accessory device that can enclose a part of gastrointestinal tract around the tip of endoscope for detailed examination of a particular portion of the gastrointestinal tract. There is need, therefore, for an accessory tool for endoscopic examination that creates an endoluminal compartment around the endoscope tip. Such endoluminal compartment can then be filled with air, water or could be thoroughly lavaged using the device. Such a device can further include balloons comprising at least a proximal balloon for maintaining the position of the endoscope accessory in an area to be examined and to seal the proximal end of the endoluminal compartment. There will be an independently positioned distal balloon on a catheter for sealing the distal end of the examination partition. The accessory device can also include a third balloon on the interior surface that creates a seal between the accessory device and endoscope to complete the endoluminal compartment. The endoscope accessory can be advanced or retracted without the need to deflate and re-inflate the balloons, thereby creating a movable endoluminal compartment. The endoscope accessory can be placed on an endoscope shaft without the necessity of having to remove the endoscope from the body. Some embodiments of the present invention provide such a device.

SUMMARY OF THE INVENTION

The present disclosure includes accessory devices for use with an endoscope or other medical device. Although variations of the device are discussed as an endoscopic accessory device, the accessory device can accommodate any number of diagnostic, therapeutic, and/or surgical devices. In one variation, the endoscopic accessory device comprises a wall structure having a proximal portion spaced in a lengthwise direction from a distal portion along an axis, the wall structure having a first edge and a second edge extending parallel to the axis in the lengthwise direction from a proximal end of the proximal portion to a distal end of the distal portion and separated by a wall structure width, the wall structure including an interior surface, an exterior surface, and an intermediate space therebetween such that a fluid can be delivered into the intermediate space to adjust a flexibility of the wall structure; a tip material located at to the distal portion and having a tip length extending distally beyond the distal end, the tip material having a tip width greater than the wall structure width; a first seam structure extending along the first edge and a second seam structure extending along the second edge; a proximal balloon located on the exterior surface at the distal portion; an inner balloon located on the interior surface and proximally spaced from the distal end; an instrument lumen extending from the proximal portion distally to the inner balloon and having an instrument lumen opening on the interior surface; and a hub portion at the proximal portion of the wall structure and on the exterior surface, the hub portion comprising at least a proximal balloon port fluidly coupled to the proximal balloon by an proximal balloon lumen, an inner balloon port fluidly coupled to the inner balloon by an inner balloon lumen, an instrument port fluidly coupled to the instrument lumen, wherein in a pre-deployment configuration the proximal balloon and the inner balloon are uninflated, and the wall structure is sufficiently flexible to assume a flat profile across the wall structure width; wherein the first seam structure can be releasably joined to the second seam structure to form a fluid tight seal therebetween such that the wall structure can form a closed overtube profile about the endoscope; wherein in the closed overtube profile the tip width of the tip material permits the tip material to circumferentially overlap distal end.

Variations of the endoscopic accessory device include a flange portion on an interior surface extending over the first seam structure such that in the closed overtube profile, the flange portion covers the first seam structure when joined to the second seam structure.

In an additional variation, a width of the inner balloon is greater than the wall structure width such that the inner balloon circumferentially overlaps the fluid tight seal on the interior surface over the endoscope when in the closed overtube profile.

The endoscopic accessory devices can include a configuration where the interior surface comprises an interior sheet of material, and the exterior surface comprises an exterior sheet of material.

The devices disclosed herein can include any number of ports or openings on the interior or exterior of the device. For example, the device can include a catheter lumen extending from the proximal portion to the distal portion and having a catheter opening on the interior surface distal to the inner balloon.

In an additional variation, the endoscopic accessory device further includes a balloon catheter having a distal balloon and slidably moveable through the catheter lumen, where the hub portion includes a catheter port fluidly coupled to the catheter lumen and a proximal end of the balloon catheter is slidably positioned in the catheter port. A distal balloon located on the balloon catheter that moves freely inside the catheter lumen and while uninflated can be stored in catheter lumen and can be extended distal to the tip of endoscope and, while inflated creates a seal at the distal end of the endoluminal compartment. Variations of the devices can include configurations where a flexibility of the distal portion is greater than a flexibility of the proximal portion. Moreover, a flexibility of the tip material is different than the flexibility of the distal portion.

The endoscopic accessory devices can include any number of adhesive regions on the tip material, such that the at least one adhesive region permits securing a first portion of the tip material to a second portion of the tip material in a conical or tubular shape.

The endoscopic accessory devices described herein can include a lubrication lumen extending from the proximal portion proximally to the inner balloon and having multiple openings inside the interior surface of the wall structure and a lubrication port on the proximal hub fluidly coupled to the lubrication lumen.

Variations of the device include when in the closed overtube profile, a portion of the tip material overlapping the distal end of the exterior sheet of the device and a portion of the first seam structure and the second seam structure.

The tip material of the accessory device can form a cylindrical shape or a conical shape at the end of the closed overtube profile.

The proximal balloon can expand to be asymmetrical about the wall structure.

The endoscopic accessory devices described herein can include any number of fluid ports and/or vacuum ports on the exterior surface of the wall structure.

As the accessory device is made from two or more layers of sheets, the two sheets can be bound by ultrasonic bonding, sewing or RF welding along its entire length, at the longitudinal edges or other spots, and over a zipper edge that acts as longitudinal seam and closes the accessory device longitudinally and turn the double layer sheets into an overtube profile. There are also multiple interspersed tacks bonding over the surface of the two sheets to hold the sheets together. The zipper is located at the edge between the two layers. As such, the two layers can accommodate the edge of the zipper that creates the longitudinal seam between the two sheets. Moreover, the zipper is waterproof.

The flexible bilayer structure of the accessory device allows the ease of compressibility of the accessory device and reshaping of the circular accessory device into a shape that can easily accommodate the passage of the accessory device over the endoscope within the gastrointestinal tract bends.

The bilayer or multilayer structure of the accessory device allows the passage of the inflation and other tubes between the layers of the sheets along the accessory device to avoid exposure and friction of these tubes with body and or endoscope. The tubes that carry the proximal balloon or endoscope accessories can exit the space between the two sheets at the distal end portion of the accessory device and enter in the endoluminal compartment.

The bilayer or multilayer structure of the accessory device allows inflation or deflation between the layers of the sheets along the accessory device to change the flexibility or rigidity of the accessory device.

The zipper alignment cutout aid can be at the distal end of the accessory device. The zipper alignment cutout aid can be covered at the distal end of the accessory device by the soft tip sheet.

Alternatively, the seam can be created by other interlocking mechanisms such as self-fusing silicon tape, tongue and groove, complementary edges, hook and loop, zip-lock-type fastener, adhesive straps, and straps and the like, or a combination of these mechanisms.

The proximal end of the accessory device is supplied with an elastomeric sealing bead or soft sealing material that, when the accessory device forms into a tube, the sealing bead forms a proximal seal between the accessory device and endoscope.

The accessory device can further include more than one elastomeric sealing bead on the internal surface of the accessory device for the creation a seal around the endoscope shaft within the accessory device. This elastomeric sealing bead on the internal surface of the flexible accessory device can be made from foam or other elastomeric material that does not allow free passage of air or fluid. The elastomeric sealing bead has a rectangular surface when the accessory device is not formed. The proximal edge of the elastomeric sealing bead can have a ramp that allows ease of passage of endoscope that enters the proximal end of the elastomeric sealing bead when the accessory device is formed. The elastomeric sealing bead can have the same height across the transverse span of the accessory device, so when the accessory device has formed the edges of the elastomeric sealing bead touch each other at the level of the seam when the longitudinal edges are approximated. Alternatively, the elastomeric sealing bead can have a ramp toward the longitudinal edges. This gradual decrease in the height of the elastomeric sealing bead allows the elastomeric sealing bead to take an eccentric shape when the accessory device is formed. This allows a better seal created by the elastomeric sealing bead over the endoscope. The elastomeric sealing bead seals the accessory device around the endoscope to prevent the leakage of fluid and gas from the proximal end of the accessory device. Alternatively, the elastomeric sealing bead can be positioned on the internal surface of the accessory device at the mid portion or proximal end portion of the accessory device. Alternatively, there could be more than one elastomeric sealing bead within the internal surface of the accessory device.

In additional variations, the inner balloon can be positioned on the internal surface of the accessory device at the mid portion or proximal end portion of the accessory device. Alternatively, there could be more than one inner balloon and one or more elastomeric sealing bead all installed within the internal surface of the accessory device.

The endoscope accessory can also include at least one irrigation/drainage port. The irrigation/drainage port can be situated on the accessory device hub and can include a closeable lid. The irrigation/drainage port can allow a direct access to the lumen of the accessory device. The irrigation/drainage port can be connected to irrigation/drainage tubes that can deliver water into or drain water out of the examination compartment in the gastrointestinal tract through the lumen of the accessory device.

The accessory device can further include at least one fluid/insufflation conduit that defines a passageway for inflating or suctioning fluid or air within the endoluminal compartment within the body cavity at the distal end of the accessory device.

The accessory device can further include more than one instrument lumen that defines a passageway for passing accessory tools from the proximal end of the accessory device into the endoluminal compartment within the body cavity at the distal end of the accessory device.

The accessory device can further include at least one quick connect fitting. The quick connect fitting allows a detachable coupling of multiple tubes at the proximal end portion of the accessory device into an umbilical extension tube. The umbilical extension tube has one quick connect fitting on each end and serves as an extension tubing to connect the accessory device to inflation, irrigation, insufflation, or suction devices. The male-female interface of the quick-connect fitting allows a detachable connection of multiple ports and tubes with one locking action. Examples of the ports and tubes that can be detachably attached through the quick connect fitting can include but not limited to inflation tube for positioning ring, inflation tube for sealing band/s, inflation tube for distal balloon, insufflation port for insufflation with gas, irrigation tube for flushing port, suction conduits and fluid/insufflation conduit.

The accessory device can further be supplied with an automated control system for automated control of inflation, insufflation, irrigating, and suctioning through the overtube. The automated control system can control the inflation of the proximal balloon, inner balloon, distal balloon, insufflation of the compartment, injection or irrigating fluid into the irrigation drainage port, irrigation conduit of flushing port, and suctioning of the suction conduits. The automated control system can inflate and maintain each individual balloon pressure at an assigned set point, insufflate and maintain the endoluminal compartment pressure at an assigned set point, inject fluid into the assigned port, and apply suction pressure to an assigned conduit. The activation and set points of the functions are adjusted through knobs or digital displays. In an additional variation, the system can have a manual control system for inflation, insufflation, irrigating, and suctioning through the overtube.

In use, the endoscope accessory of the claimed invention is a flexible, elongated sheet or sheets that envelops an endoscope shaft while the endoscope shaft is still within the body cavity without the need to remove the endoscope or pre-position the accessory device over the endoscope shaft prior to the endoscope being inserted within the body cavity.

After enveloping or surrounding the endoscope shaft by the sheet or sheets, the opposing longitudinal edge portions can be joined to form an accessory device by creating a longitudinal seam along a portion or the entire length of the accessory device.

The accessory device seam joins together starting at the tip portion resulting in a closed distal end portion of the accessory device. The tip portion can then be secured with at least one adhesive region over the distal end portion of the wall structure and joined seam. The accessory device seam can extend further along the accessory device's length or along a partial length. When an endoscope shaft is enveloped within the accessory device, the hub of the accessory device can be grasped and the distal portion of the accessory device pushed into the body cavity of a patient with the guide of the endoscope shaft placed at the desired location. The accessory device can advance just proximal to the tip of the endoscope. In some variations of the accessory device, the device seam is closed starting from the distal end to a portion of the device to form a closed overtube shape. The closed overtube shape can be inserted inside the colon while the seam of the more proximal part of the accessory device remains open outside of the body cavity.

The inflatable proximal balloon is inflated to secure the position of the accessory device distal end portion within the body cavity and create a seal between the accessory device and body cavity, proximally.

The balloon catheter is pushed through the catheter lumen and after the distal balloon exits the catheter lumen at the distal tip of the accessory device, it is placed at the desired location, distal to the distal tip of the endoscope. Then, the distal balloon is inflated. This secures the position of the distal balloon within the body cavity and also seals the distal portion of the endoluminal compartment.

Then the inner balloon is inflated that can create a seal around the endoscope shaft within the accessory device. The endoscope can be moved independent of the accessory device while the sealing is maintained. The endoscope can be replaced if desired, with another endoscope while the accessory device stays in its position within the body cavity.

The endoluminal compartment can be filled with any fluids, including but not limited to air, $CO_2$, or water and the pressure of the compartment can be controlled using manual valve, pressure relief valve and automatically controlled pressure system, depending on applications. In addition, the endoluminal compartment can be thoroughly lavaged using the irrigation tubes connected to irrigation/drainage port or the proximal accessory device opening.

The endoluminal compartment can be made smaller or larger by changing the position of the distal balloon by pushing or pulling the accessory device while maintaining the inflated proximal balloon without the need for deflation.

The endoluminal compartment can be moved along the body cavity, by pushing or pulling the entire accessory device without the need for deflation of the distal balloon, proximal balloon, or inner balloon.

When the endoluminal compartment is moved along the body cavity, it maintains its pressure and its content of air or water based on the application. This allows the endoscope to examine an extended part of the gastrointestinal tract as the location of the endoluminal compartment glides over the intestinal lumen. At the preference of the user, the movement can be stopped or reversed.

When the compartment is moved along the body cavity, since the balloons are passing part of gastrointestinal tract with different diameters and tones, the pressure in the balloons needs to be monitored and adjusted to make sure the size of balloons properly fit the size of the gastrointestinal tract lumen. This is performed with monitoring of the balloon pressures.

When the compartment is moved along the body cavity while the balloons are inflated, the movement of the inflated balloons along the gastrointestinal lumen creates a squeegee action and wipes fluid secretion and residuals away from the intestinal wall. This allows physical cleaning and wiping of the intestinal lumen before examination by the endoscope. This is particularly important when the inflated proximal balloon wipes the intestinal wall off of fluid and residuals when the accessory device is pulled out of the body cavity.

When the compartment is moved along the body cavity while the balloons are inflated, the squeegee action of the balloons wipes the intestinal wall off of fluid secretion and residuals away from the moving compartment. During this movement, the flushing port situated on the external surface of the accessory device between the inflatable proximal balloon and the proximal end portion of the accessory device is used to inject fluid to flush the body cavity proximal to the proximal balloon. This enhances the cleaning squeegee action of the proximal balloon.

The examination compartment can be used as a sealed compartment for possible surgeries or access to spaces outside of gastrointestinal tract. In that case, after inflating the proximal and distal balloon, the endoscope can be removed, and other surgical device/s is/are placed within the endoluminal compartment. The surgical devices can be used for examination of peritoneum or to perform intraperitoneal surgeries.

The proximal, distal and inner balloons can be deflated and inflated independently of each other or together as determined by the user.

After termination of the examination, all balloons are deflated, and the overtube is removed independent of, or together with, the endoscope.

The present disclosure also includes methods of preparing a colon for examination. In one example, the method includes advancing an endoscopic device within the colon; advancing an endoscopic accessory device over the endoscope, the endoscopic accessory device including a first balloon adjacent to a distal opening; expanding the first balloon against a wall of the colon; positioning a balloon catheter through the distal opening such that a second balloon on the balloon catheter is spaced from the distal opening; delivering a fluid through the endoscopic accessory to the colon; expanding the second balloon against the wall of the colon; and withdrawing the first balloon and the second balloon while engaged against the wall of the colon to prepare the colon for examination.

Another variation of the method can include advancing an endoscopic within the colon; advancing an endoscopic accessory device over the endoscope, the endoscopic accessory device including a first balloon adjacent to a distal opening; expanding the first balloon against a wall of the colon; positioning a balloon catheter through the distal opening such that a second balloon on the balloon catheter is spaced from the distal opening; delivering a fluid through the endoscopic accessory to the colon by positioning a fluid reservoir at above the endoscopic accessory such that gravity causes the fluid to flow into the colon; draining the fluid from the colon by lowering the fluid reservoir below the endoscopic accessory such that gravity causes a portion of the fluid to drain into the fluid reservoir; and expanding the second balloon against the wall of the colon and withdrawing the second balloon towards the distal end to cause the fluid to enter the distal opening and to prepare the colon for examination.

DETAILED DESCRIPTION OF THE INVENTION

Before explaining some aspects of embodiment of the present invention in detail, it is to be understood that the present invention is not limited in its application to the details of arrangements of the components set forth in the following description. As can be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention, and for example, they are approximate ranges and are not to be limiting except where noted otherwise.

Figure 1:
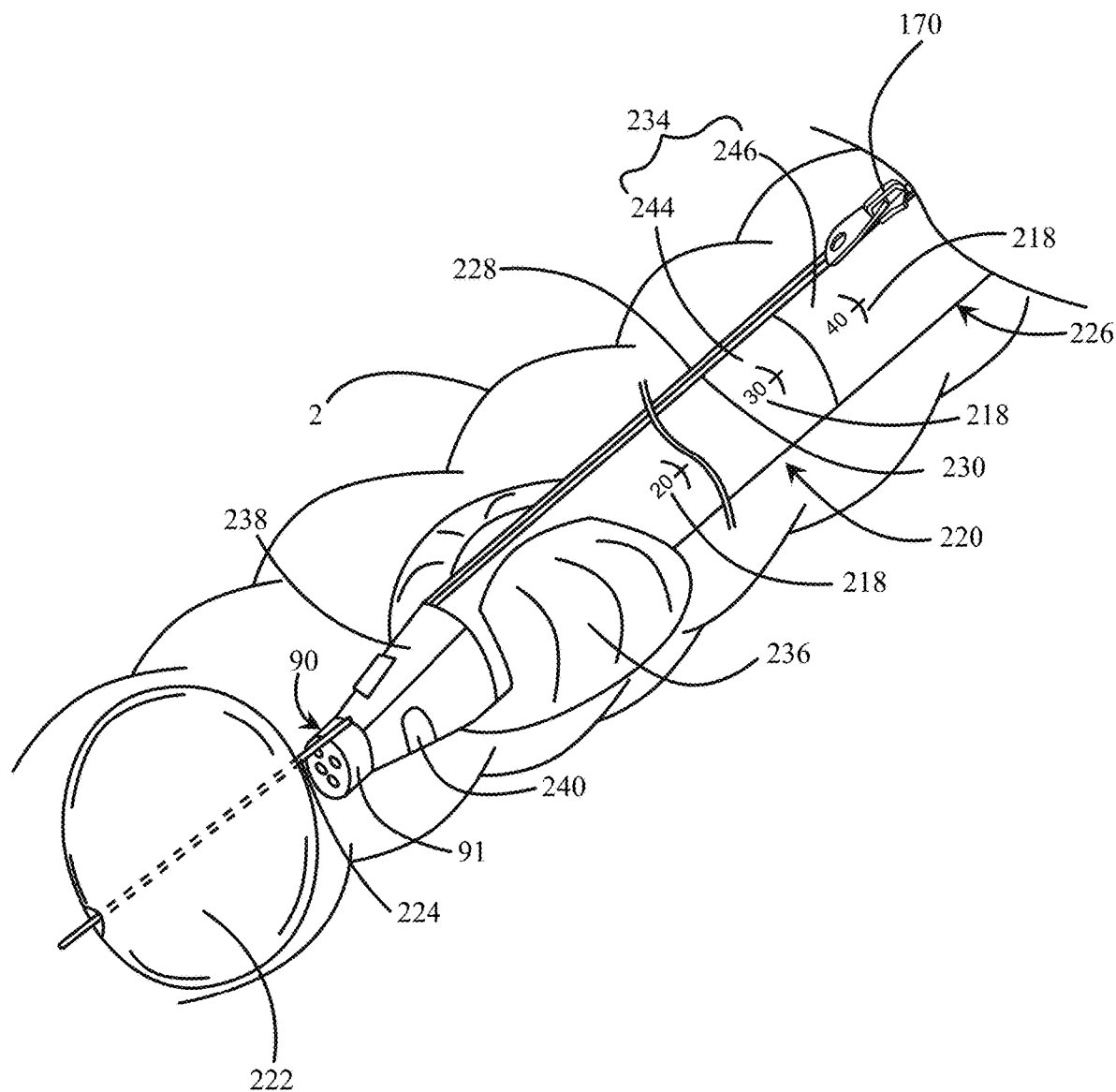
FIG. 1 illustrates a variation of an endoscopic accessory device being advanced within a body cavity.

FIG. 1 illustrates a variation of an endoscopic accessory device 220 advanced within a body passage 2 (e.g., a colon, gastrointestinal tract, or other body passage), where the device 220 includes a distal balloon 222 and proximal balloon 236, as discussed above. While the illustrated variation is shown with an endoscope 90, any medical device can be used within the endoscopic accessory device 220. Examples of inserted devices include examination devices (such as scopes), as well as treatment or therapy devices.

For purposes of illustration, the proximal balloon 236 is in an inflated configuration state while the distal balloon 222 is inflated to expand from a balloon catheter 224. The location of the proximal balloon 236 is intended for illustration only, and variations include one or more proximal balloons 236 spaced farther away from the distal tip 238.

The proximal balloon 236 can be used for positioning the device 220 within the body. Alternatively, or in combination, the proximal balloon 220 can be used to clear the organ, as further discussed below. Variations of the device 220 include an examination compartment formed between the distal balloon 222 and proximal balloon 236. This examination compartment can be moved along the body cavity 2 when the accessory device 220, shaft 91 and the distal balloon 222 are all moved as a single unit in relation to the body. This movement can occur without deflating the distal balloon 222 or proximal balloon 236. Alternatively, either or both of the balloons 222 236 can be deflated, repositioned, and reinflated as needed to establish an examination compartment at a desired location or to irrigate/clean the body passage 2.

In the illustration shown in FIG. 1, the endoscopic accessory device 220 includes a body structure 226 comprising a wall structure, as discussed below. In the example shown in FIG. 1, the body structure 226 is in a tubular shape where a first seam 228 joins with a second seam 230, where the seams are located on the ends of the body structure 226. The exterior surface of the device 220 can include any number of features that assist the caregiver in advancing the device 220. For example, the variation shown in FIG. 1 includes distance markings 218 that can be used to monitor advancement of the device 220 within the body passage 2 or relative to the endoscope shaft 91. The device 220 can have a length that is greater than, less than, or equal to the inserted device. However, devices 220 varying lengths are within the scope of this disclosure. As shown, the device 220 can be opened along an entire seam of the device 220 such that it can be placed over a medical without removal of the medical device. Alternatively, the accessory device may be used while the seam is only closed at the distal portion and the remains open at the proximal portion to accommodate smaller endoscopes while the accessory remains fully functional.

In variations of the device 220, the body structure 226 includes an outer surface 234 with a distal portion 244 and a proximal portion 246, each having different properties or characteristics. For example, the distal portion 244 can have a greater flexibility than the proximal portion 246. This increased flexibility improves the ability of a caregiver to navigate the tubular body 226 through tight bends and turns within the anatomy. Similarly, the proximal portion 246 can be less flexible or stiffer, which increases pushability of the tubular body 226 from a working end, handle, or any part of the device that is outside of the patient. It is noted that the distal portion 244 and proximal portion 246 can be constructed from various layers of materials such that the distal portion 244 and the proximal portion 246 comprise the same material on an outside surface 234 of the device 220. In such a variation, the interior surface or the region within a wall structure of the distal portion 244 can comprise materials and/or structural features that cause the distal portion 244 to be more flexible than the proximal portion 236.

The tubular body 226 also includes a distal tip 238 that encloses around an endoscope shaft 91 while allowing the endoscopic accessory device 220 to slide relative to the endoscopic shaft 91. In variations of the device, the distal tip 238 can include a length that is sufficient for an end 240 of the tip 238 to wrap around the tubular body 226. As discussed herein, the shaft 226 of the endoscopic accessory device 220 includes a first seam structure 228 and a second seam structure 230 that join together to allow the device 220 to form the tubular structure 226 from a planar configuration. Variations can include any number of fluid delivery or suction ports on an exterior of the device 220. FIG. 1 also illustrates an optional zipper mechanism 170 that can be used to close the seam structures 228 230 together starting at a distal end of the device 220.

Figure 2A:
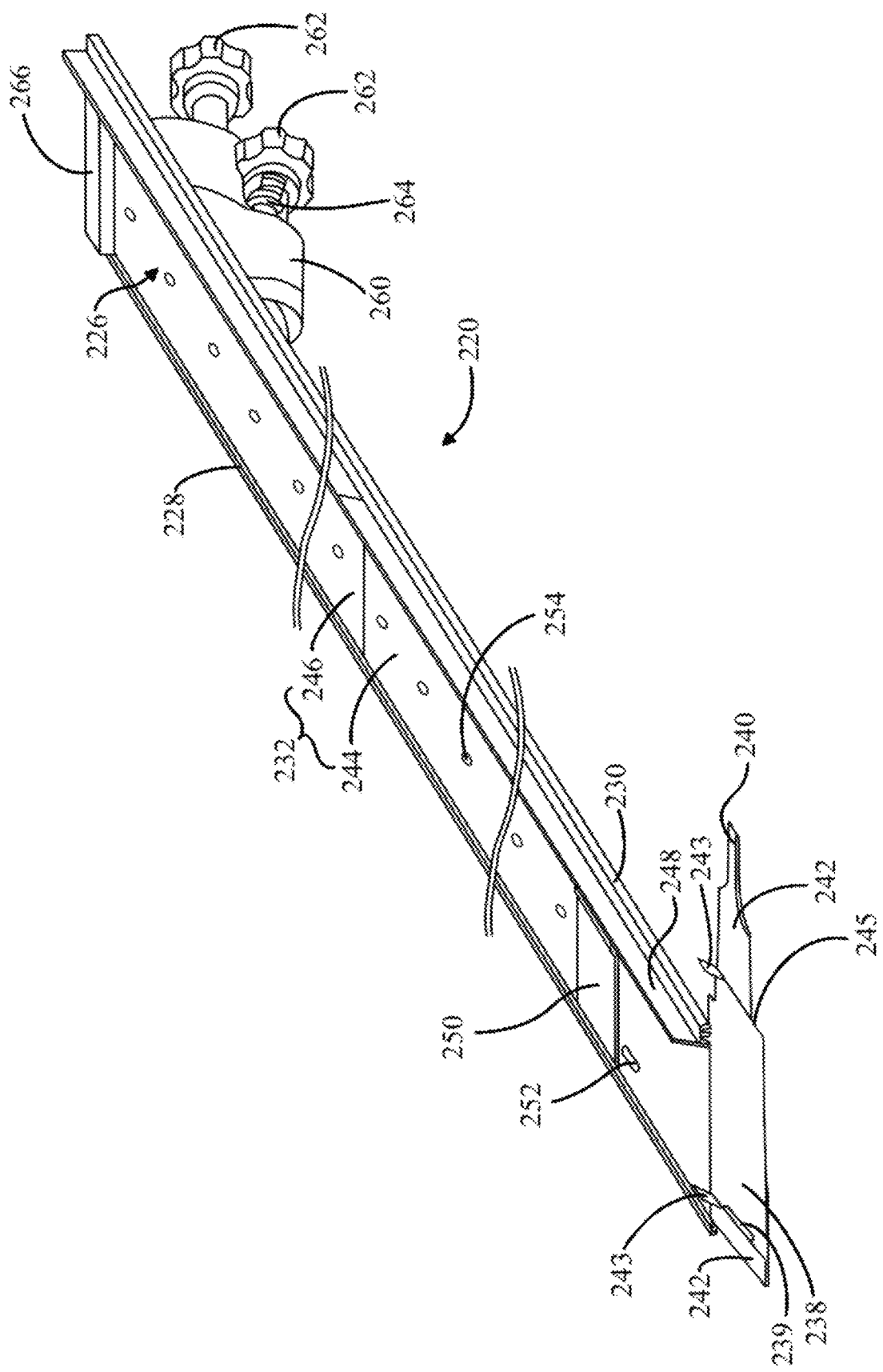
FIG. 2A illustrates the endoscopic accessory device of FIG. 1 prior to the joining of the seam structures for forming the tubular body structure.

FIG. 2A illustrates the endoscopic accessory device 220 of FIG. 1 prior to joining of the seam structures 228 230 for forming the tubular body structure 226. The first seam structure 228 extends along an edge of the wall of the body structure 226, and the second seam structure 230 extends along the opposite edge of the wall of the body structure 226. As shown, the body structure 226 can assume a flat configuration where an inner surface 232 includes a distal region 247 and a proximal region 246 having different flexible properties, as noted above. In additional variations, the inner surface 232 can comprise a single material/property where the varying degrees of stiffness are controlled by selection of the outer surface 234 (as shown in FIG. 1). As discussed below, the body structure 226 wall can be formed by separate layers (e.g., the outer surface 234 and inner surface 232 each comprises a different layer). Alternatively, the body structure 226 wall can comprise a single material having passages/lumens formed within the wall.

FIG. 2A also shows an interior flap 248 extending along the sealing structure 230. This flap 248 can comprise an extension of the inner layer 232 or can be a separate section of material sealingly joined to the inner layer 232. As noted below, the flap 232 overlaps the joined sealing structures 228 230 when the body structure 226 is in a tubular configuration. The combination of the sealing structure 228 230 and adhesive region 242 allows for the body structure 226 to be fluidly sealed along the joined edges 228 230. The figures show the adhesive region 242 with tab 243 allows removal of a cover from the adhesive regions 242.

FIG. 2A further shows the interior surface 232 to include a plurality of lubrication openings 254. These lubrication openings 254 allow for a medical caregiver to deliver water or lubrication fluid to the interior of the body structure 226 when formed into a tubular shape, which allows for the endoscopic accessory device 220 to slide over a body of an endoscope. In an additional variation, the inner surface 232 of the accessory device 220 can comprise a lubricious material or a material with a hydrophilic coating or a hydrophobic coating. In such a case, the ports 254 deliver a fluid (e.g., water or saline) to activate the hydrophilic coating, which reduces friction between the inner surface 232 and any medical device advanced through the accessory device 220 with or without the use of additional lubrication. The wall structure 226 can be configured such that a fluid can be delivered between the interior surface and exterior surface (i.e., between the layers) to adjust a flexibility or rigidity of the wall structure when flat or when in an overtube shape.

The distal portion of the body structure 226 also includes an inner balloon 250 in an uninflated configuration as well as a proximal balloon (not shown) on the opposite side of the device 220 in an uninflated configuration. As discussed herein, the body structure 226 can incorporate any number of passages or lumens to fluidly couple the balloons 236 250, openings 254, suction channels, irrigation channels, or working channels 252 (e.g., for a balloon catheter) with ports or other fittings 262, 264 on a hub 260 on a proximal end of the device 220. In one variation, one or more of the passages are formed from tubular structures located within the body structure 226. These tubular structures can provide further column strength when advancing the device 220 over an endoscope.

In some variations of the device, the hub 260 can function as a handle for manipulating the device. Alternatively, the main function of the hub 260 can serve as a location for ports and or connectors 262, 264. Such connectors and ports can include coupling for external inflation tubes, quick connect fittings, distal balloon quick connect fittings, and irrigation/drainage ports, as well as delivery of various medical tools through the device 220.

FIG. 2A also shows an example of a distal tip 238 that can enclose about an endoscope when in use. The distal tip 238 can comprise a flexible material such that the flexibility of the tip 238 is greater than the flexibility of the adjacent interior wall section 232/244. As shown in FIG. 2A and discussed below, the distal tip comprises a width (i.e., as measured perpendicular to a length of the device 220) that exceeds a width of the body structure 226 and sealing structures 228 230. This allows the tip 238 to form a cylindrical or conical shape at the end of the device 220 when formed into a tubular structure. In one variation, the belt 240 is inserted into an opening/slot/slit 239 in the tip 238. Variations of the device 220 include an opening slit 239 that is positioned relative to a shoulder 245 of the tip 238 such that when formed into a cylindrical/conical shape the shoulder 245 limits the diameter of the enclosed tip 238 to prevent over-tightening of the tip 238 onto an endoscope. Accordingly, the opening slit 239 and shoulder 245 can be spaced to accommodate a standard size endoscope or can have multiple openings to accommodate endoscopes of various sizes. In addition, the tip 238 can include any number of adhesive regions 242 with an adhesive removeable covers. For example, in the variation shown in FIG. 2A, the ends of the tip 238 include adhesive regions 242 (e.g., a removable cover) that exposes the adhesive regions 242) to secure both ends of the tip 238 when formed into a cylindrical or conical shape. In the illustrated drawing, the adhesive region 242 adjacent to the opening slit 239 includes a tab section 243 that is unattached to the tip 238 and the adhesive region 242, which allows a user to expose the adhesive region 242 to adhere to a portion of the tip. Likewise, the belt 240 of the tip includes an adhesive region with a tab 243 that allows removal of a cover.

FIG. 2A illustrates the endoscopic accessory device 220 having an elastomeric sealing bead or barrier 266 located at a proximal portion of the body structure 226. The barrier 266 can extend across the width of the body structure 226 and optionally over the lip 248. The barrier 266 can comprise a non-porous foam that creates a barrier to fluids that would otherwise leak out of the proximal end of the device 220. Alternatively, the barrier 266 can comprise an absorbent foam material or other elastomeric material.

Figure 2B:
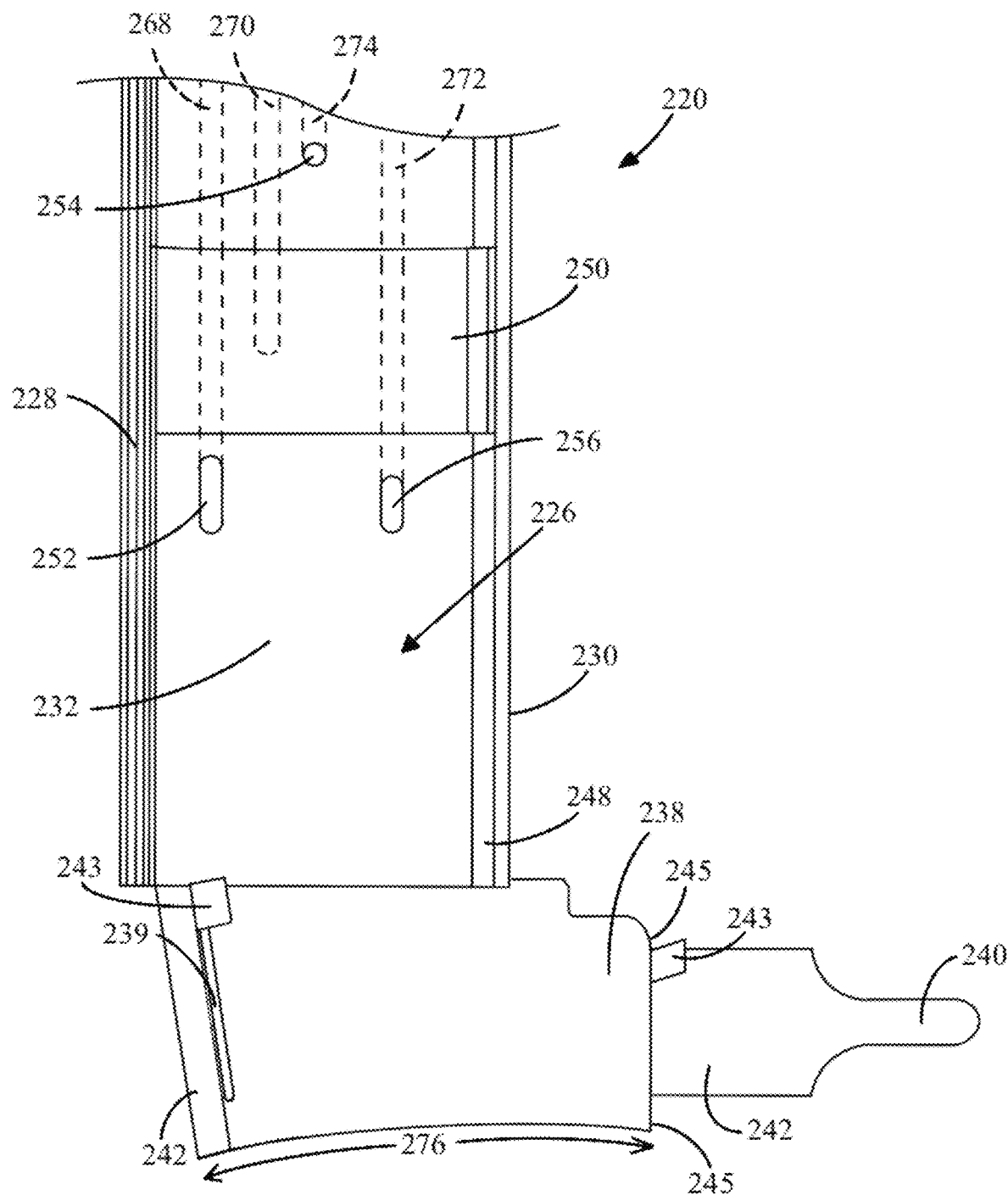
FIG. 2B illustrates a top view of a distal portion of the device of FIG. 2A.
Figures 2C, 2D:
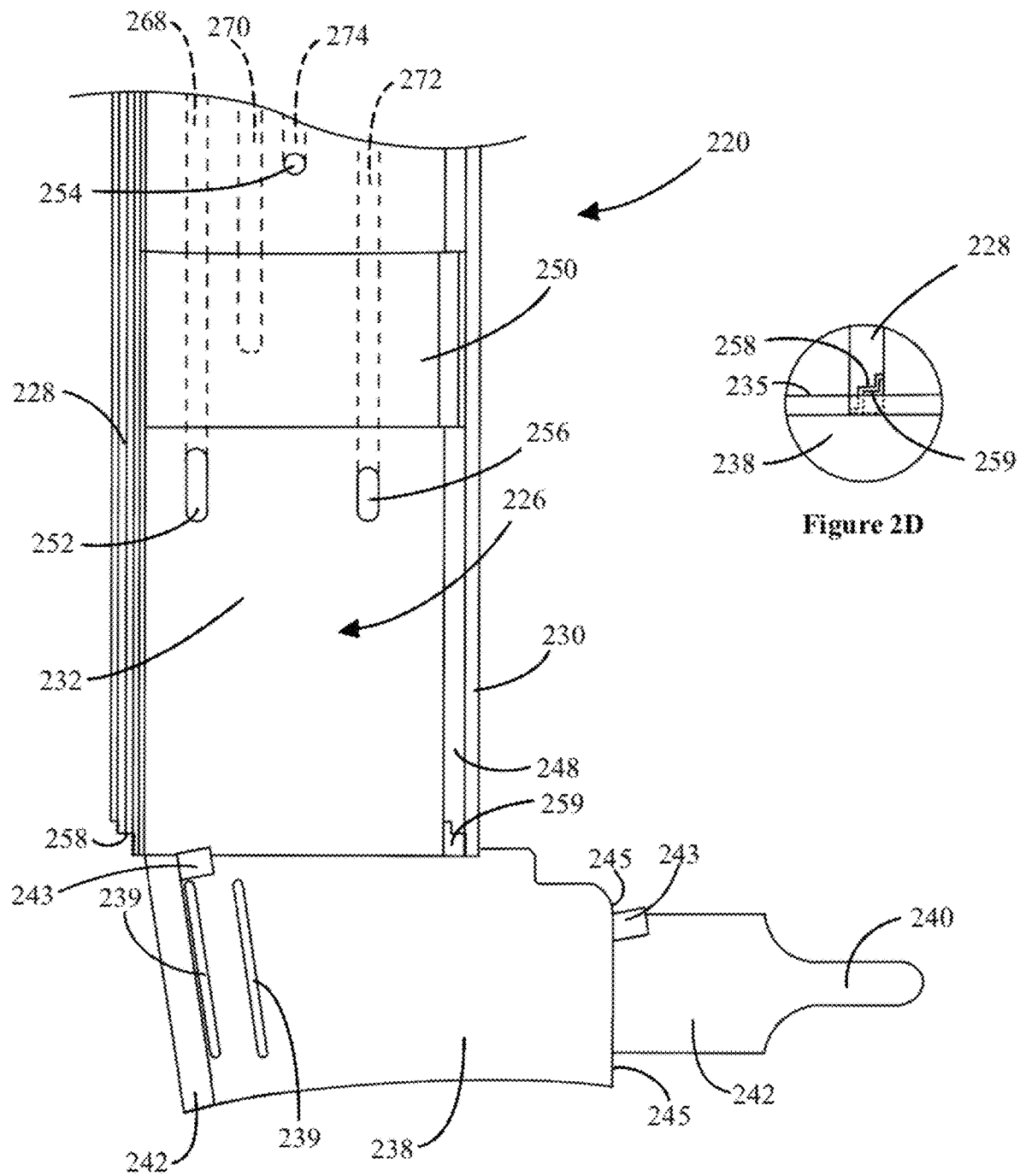
FIG. 2C illustrates a top view of another variation of a distal portion of an endoscopic accessory device.
FIG. 2D illustrates a partial view of when the first seam structure is fastened to a second seam structure with alignment features for aligning the seam structures.

FIGS. 2B and 2C illustrate top views of distal portions of variations of endoscopic accessory devices 220 similar to that shown in FIG. 2A. Both Figures illustrate a plurality of lumens or tubes 268, 270, 272, 274 that are in fluid communication with various components of the device 220. As noted above, variations of the device 220 can include a solid section of material with lumens manufactured into the material. Alternatively, the wall structure 226 can include an outer layer (not shown in FIGS. 2B and 2C) and an inner layer 232 having a plurality of tubes or structures 268, 270, 272, 274 extending between the layers. In the variations shown, tube 268 terminates at an opening 252 for the distal balloon catheter shown in FIG. 1, tube 270 provides fluid for inflation of the inner balloon 250, tube 274 delivers lubrication fluid to lubrication ports 254, tube 272 is coupled to instrument opening 256 for passage of endoscopic instrument tools. The proximal balloon and associated tube are not shown in FIGS. 2B and 2C. Clearly, any additional number of tubes and/or openings or balloons are within the scope of this disclosure.

FIG. 2B further illustrates how the placement of an opening slit 239 on a tip 238 can be positioned relative to a shoulder 245 of the tip 238 to control a opening diameter of the tip 238 such that the tip 238 is not large or over-tightened on an endoscope. As shown, the opening 239 is spaced from the shoulder 245 by a distance 276 along an edge of the tip 238. This distance corresponds to the circumference of the tip 238 that will prevent the tip opening being too large or over-tightening on an endoscope. FIG. 2C illustrates a variation with multiple openings 239 to allow the device 220 to work with endoscopes of different diameters. It is also noted that the openings 239 and shoulder 245 are positioned at an angle to a longitudinal axis of the body structure 226. This allows for the tip 238 to form a conical shape (as shown in FIG. 1). The conical shape allows for advancement of the device 226 through the body passage as opposed to an abrupt transition given the difference in sizes between the endoscope and wall structure 226 when formed into a tubular shape.

FIG. 2C also illustrate an additional variation of a device 220 where the first seam structure 228 and second seam structure 230 have respective alignment surface features 258 259 on a distal end. In the illustrated variation, alignment feature 258 is a stepped cutout, while alignment feature 259 is a stepped shoulder. When the seam structures 228 and 230 are joined together, the alignment features 258 259 nest together to ensure that the ends of the seam structures 228 and 230 are not misaligned or offset when joined together. Moreover, the alignment features 258 259 can simply make it easier/quicker for a caregiver to form the body structure 226 into a tube shape over an endoscope/medical device.

FIG. 2D illustrates a partial view of when the first seam structure 228 is fastened to a second seam structure (not visible in FIG. 2D because it is below the first seam structure 228). As shown, the alignment feature 258 of the first seam structure 228 nests with the alignment feature 259 of the second seam structure. FIG. 2D also illustrates a proximal end 235 of the tip 238 covering an end of the seam structure 228. As noted herein, variations of the device 220 provide for the tip 238 to wrap over the seam structure 228, to reduce the chance that the abrupt edge of the seam structure 228 encounters resistance when advanced in a body passageway. It also shows the proximal edge 235 of the tip 238 cover the distal end of exterior sheet 234.

Figure 3A:
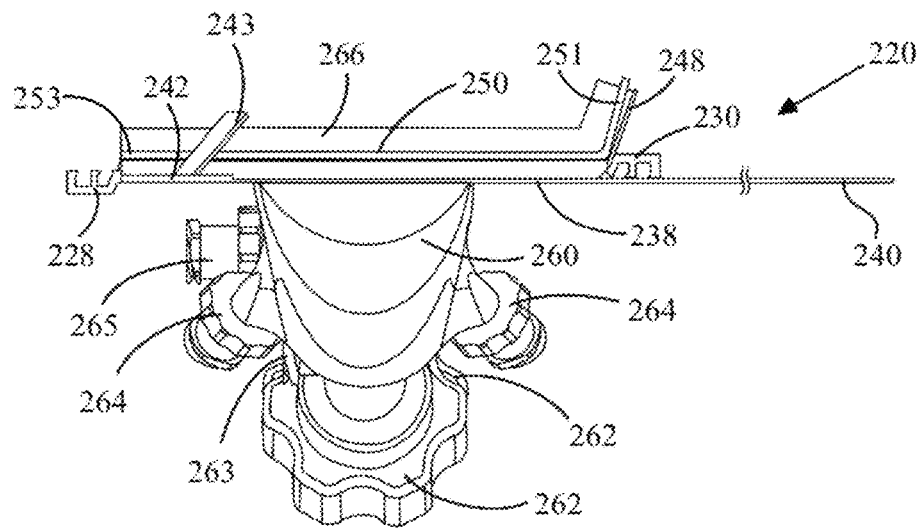
FIGS. 3A and 3B show respective front and rear views of a variation of an endoscopic accessory device similar to that shown in FIG. 2A.
Figure 3C:
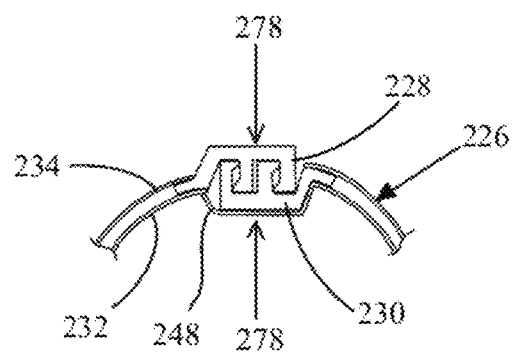
FIG. 3C depicts a variation of the sealing structures when joined together.
Figure 3B:
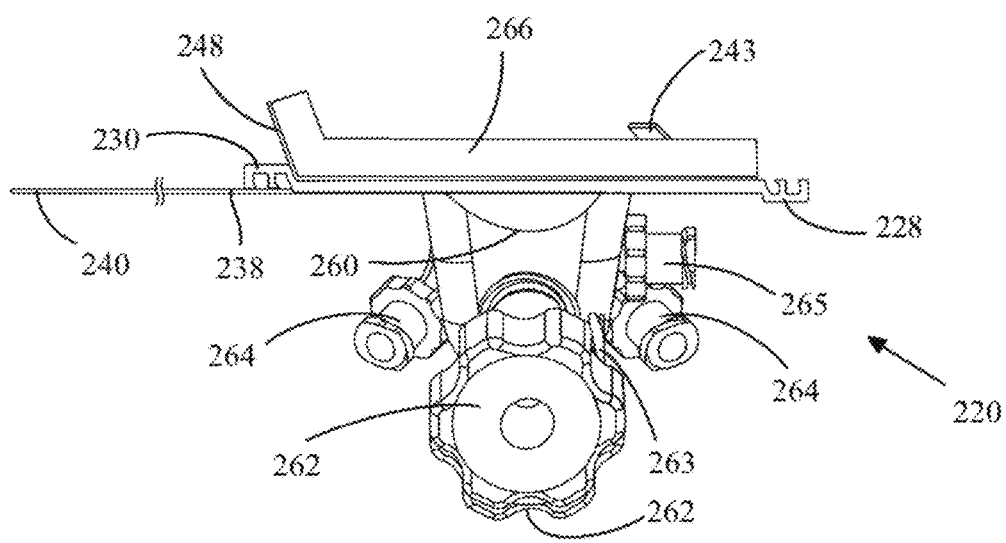

FIGS. 3A and 3B show respective front and rear views of a variation of an endoscopic accessory device 220 similar to that shown in FIG. 2A. For purposes of illustration the proximal balloon (236 in FIG. 2A) is deflated. FIG. 3A shows the hub 260 of the device 220 having a number of ports and connectors (e.g., 262, 263, 264, 265) that allow access to the various lumens, openings, and balloons of the device 220. The ports and connectors can comprise standard luer fittings and tuohy borst adapters commonly used in medical applications. In addition, one or more of the connectors 262, 264 can include flush ports 263 that allow a user of the device 220 to deliver lubrication or other fluid while advancing a device through a port 262, 264. FIG. 3A also illustrates the adhesive region 241 and adhesive removable cover 242 having a flap or tab 243 that allows removal of the adhesive removable cover 242 to expose an adhesive region 241 that secures the tip 238 into a conical or tubular form. While not shown in FIG. 3A, the belt 240 of the tip 238 can also optionally include an adhesive region.

FIGS. 3A and 3B also show a variation of a first seam structure 228 and a second seam structure 230. As shown, the seam structures can include any structure that allows for removably locking the seam structures 228, 230 together. FIG. 3C illustrates a partial view of seam structures 228 230 joined together to allow wall structure 226 to form a tubular shape where the inner surface 232 is interior to the tube shape and the outer surface 234 on an exterior of the tube. FIG. 3C also depicts a variation of the sealing structures 228 230 as joining together in directions 278, which is normal/radial direction relative to the tubular shape of the body structure 226. Since the body structure 226 is flexible, a user can apply force directly on the first seam structure 228 and through the wall structure 226 on the second seam structure 230. FIG. 3C also shows the interior flap 248 covers the seam structure 230 on an interior of the structure 226. The combination of the flap 248 and the seam structures 228 and 230 increases the ability of the device 220 to have a fluid-tight seam.

FIG. 3A also shows a variation of the inner balloon 250 extending along the interior surface of the wall structure. As shown, the inner balloon 250 can include an end portion 251 that can extend over the flap 248 or beyond the flap 248. In the illustrated variation, the internal balloon 250 extends over the second seam 230 with two ends 251 and 253, but the end 251 can extend beyond the seam 230 and cover the first seam 228 and touch the end 253 of the balloon 250 or overlap the end 253 of the balloon 250. As noted, the end portion 251 of the internal balloon 250 is shown as being unattached to the inner flap 248. Alternate variations include the end portion 251 balloon being attached to the flap 248. In additional variations, the inner balloon 250 can include a width equal to the wall of the body portion 226 (e.g., between the seam structures 228 230).

Figure 3D:
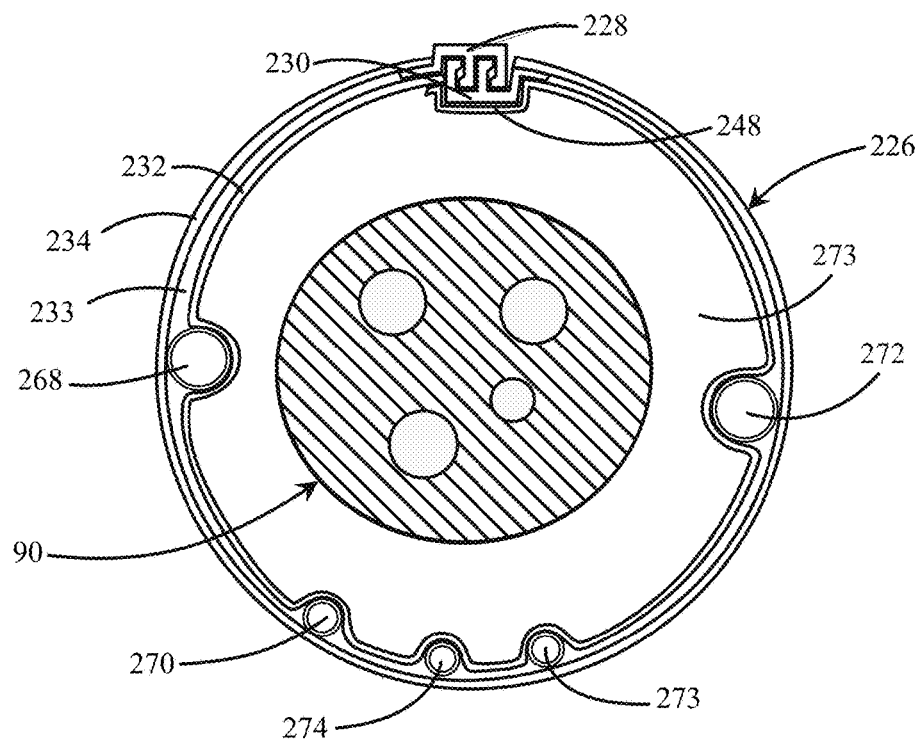
FIGS. 3D and 3E illustrate a cross-sectional view of the wall structure 226 of the accessory device.
Figure 3E:
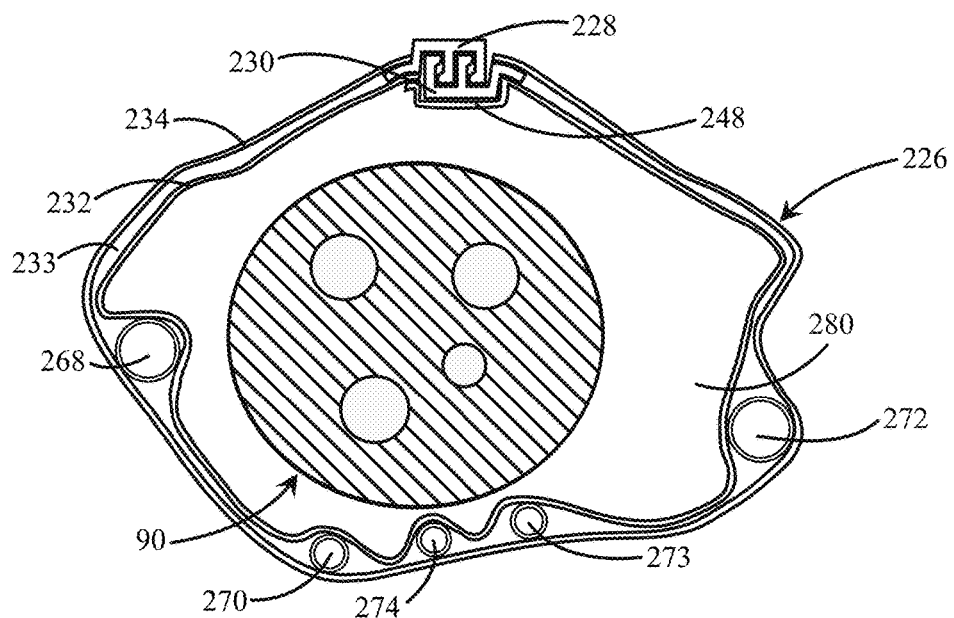

FIGS. 3D and 3E illustrate a cross-sectional view of the wall structure 226 of the accessory device. As shown, seam structures 228 230 can be joined together and covered by an interior flap 248 to cause wall structure 226 to form an overtube shape with an internal passage 280 that can accommodate an endoscope 90 or other devices. The illustrated ratio of the wall structure 226 to the endoscope 90 is for illustrative purposes only. The wall structure 226 can be made larger or smaller to provide a closer fit with the endoscope 90.

In the variations shown in FIGS. 3D and 3E, the wall structure comprises an inner layer 232 and an outer layer 234 with an intermediate space 233 between layers 232, 234. The intermediate space can accommodate any number of tube structures 268, 270, 272, 273, 274 that act as working lumens for the accessory device as discussed above. The tube structures 268, 270, 272, 273, 274 can be secured to either or both layers 232, 234 such that they remain stationary within the wall structure 226. In an additional variation, the intermediate space 233 can be selectively pressurized with a fluid to increase or decrease a stiffness of the wall structure 226. In such a variation, the wall structure 226 is designed such that fluid can flow between adjacent tubular structures. Alternatively, the wall structure 226 can have separate areas in the intermediate space 233 that can be individually pressurized. Alternatively or in combination, the device can be configured such that a vacuum can be applied to the intermediate space 233 to cause the inner 232 and outer 234 layers to seal together and increase a stiffness of the wall structure 226. In additional variations, the device can be configured such that inner sheet 232 is reinforced (e.g., by material selection, weld support spots, longitudinal weld lines, etc.) such that when the intermediate region 233 is pressurized, the inner diameter or lumen 280 does not become reduced or constricted. As noted herein, the internal passage 280 of the accessory device can also be selectively pressurized.

FIG. 3E illustrates a condition where the wall structure 226 is allowed to collapse or otherwise form an irregular shape about the endoscope 90. This irregular shape assists in advancing the accessory device through narrow passages or other anatomy that would be difficult to navigate. When the wall structure 226 assumes an irregular shape, one or more of the tubular structures 268, 270, 272, 273, 274 will provide sufficient column strength to advance the wall structure 226 over the endoscope/to the region of interest.

Figure 3F:
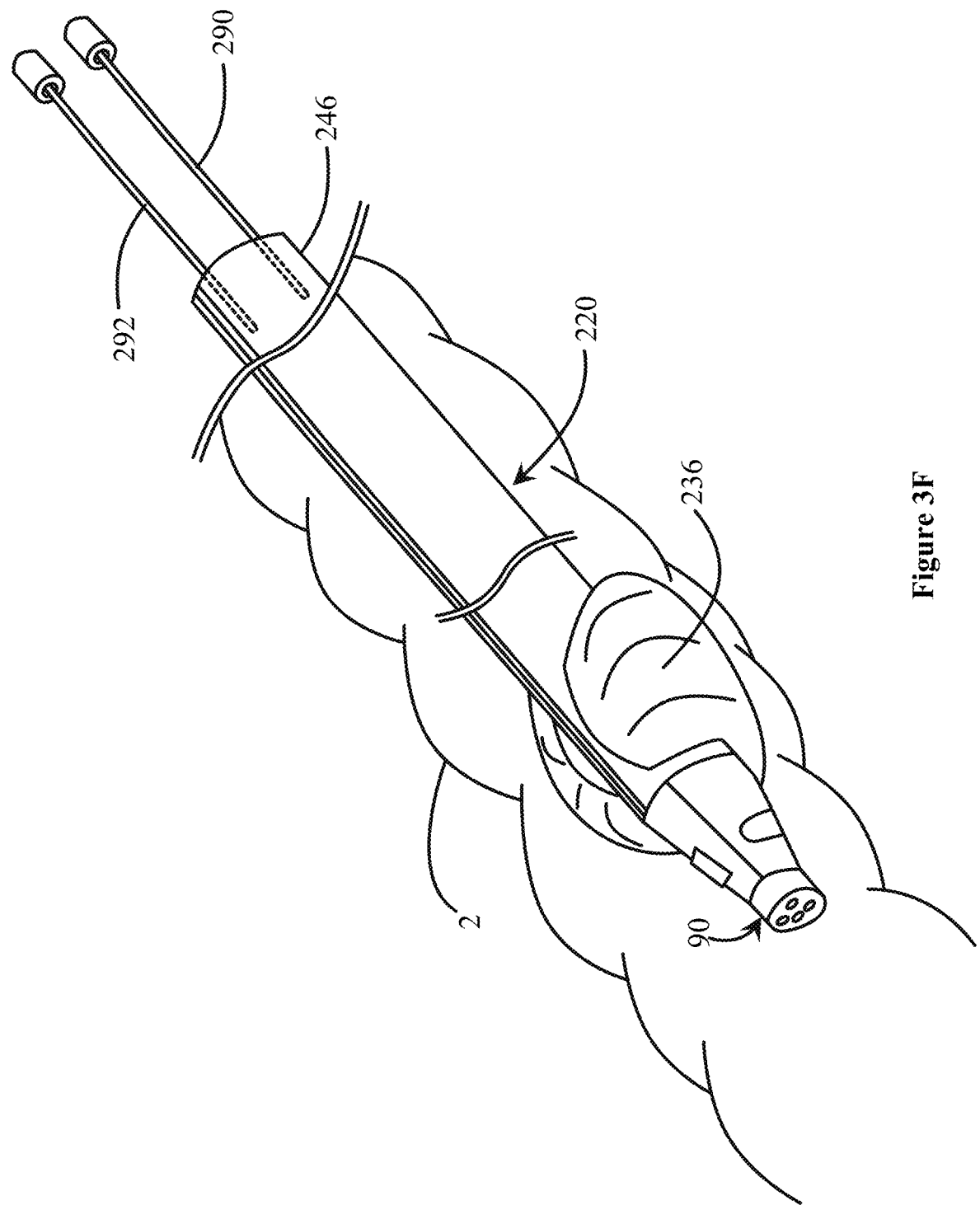
FIG. 3F illustrates a variation of a device for use with stiffener members.

FIG. 3F illustrates another variation of an accessory device 220 within a body passageway 2. In this variation, the device 220 is configured to accept one or more stiffening braces 290, 292. The stiffening braces 290, 292 can be malleable or flexible, as well having different stiffness, flexibility in different lengthwise regions. The stiffening braces 290, 292 can be inserted between an inner 232 and outer 234 layer (see FIG. 3E) or can be advanced in their own passage within the interior of the device 226. The braces 290, 292 can be used to adjust the longitudinal stiffness of the device 220 and/or to control the pushability of the device 226. Alternatively, these braces 290, 292 can be completely removed at any stage of the procedure based on the need for device 226 stiffness. While the illustration shows the stiffening braces 290, 292 inserted when the device 220 is advanced over an endoscope 90 and with the balloon 236 inflated. The braces 290, 292 can be inserted and/or removed at any state of the device 226 (e.g., prior to insertion into the body, without the endoscope, prior to balloon expansion, etc.).

Figure 4A:
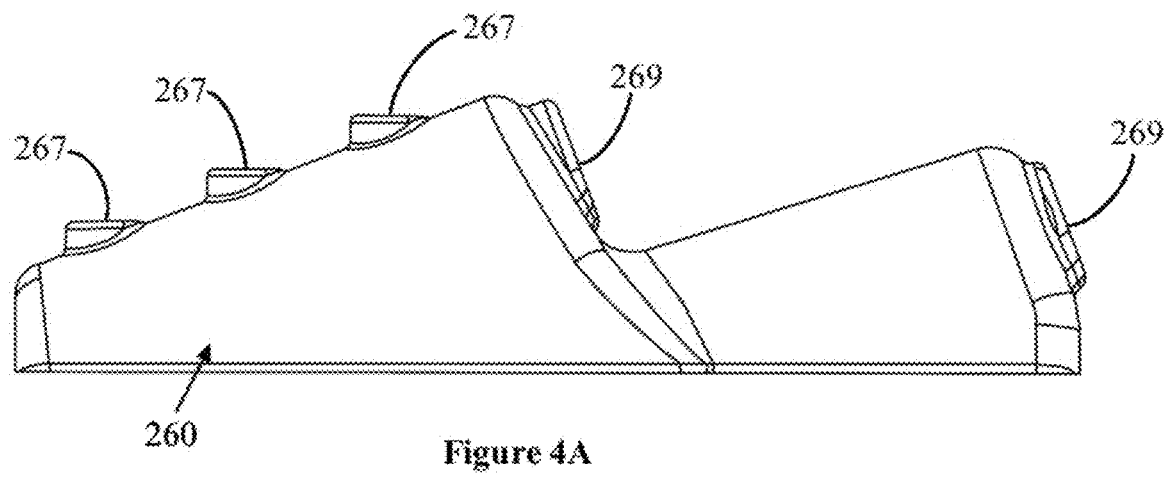
FIGS. 4A and 4B illustrate respective side and top views of another variation of a hub without the wall structure, connectors, or adaptors.
Figure 4B:
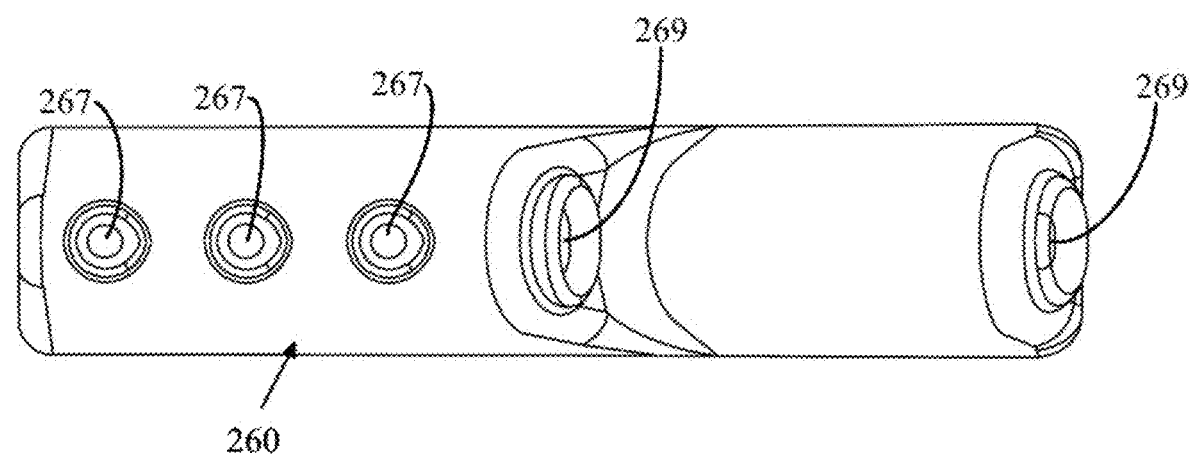

FIGS. 4A and 4B illustrate respective side and top views of another variation of a hub 260 without the wall structure, connectors, or adaptors. As shown, the hub 260 includes any number of openings 267, 269 for accessing the various lumens and passages within the wall structure as discussed above. In the variation shown in FIGS. 4A and 4B the openings 267, 279 are aligned along the hub 260.

Figure 5A:
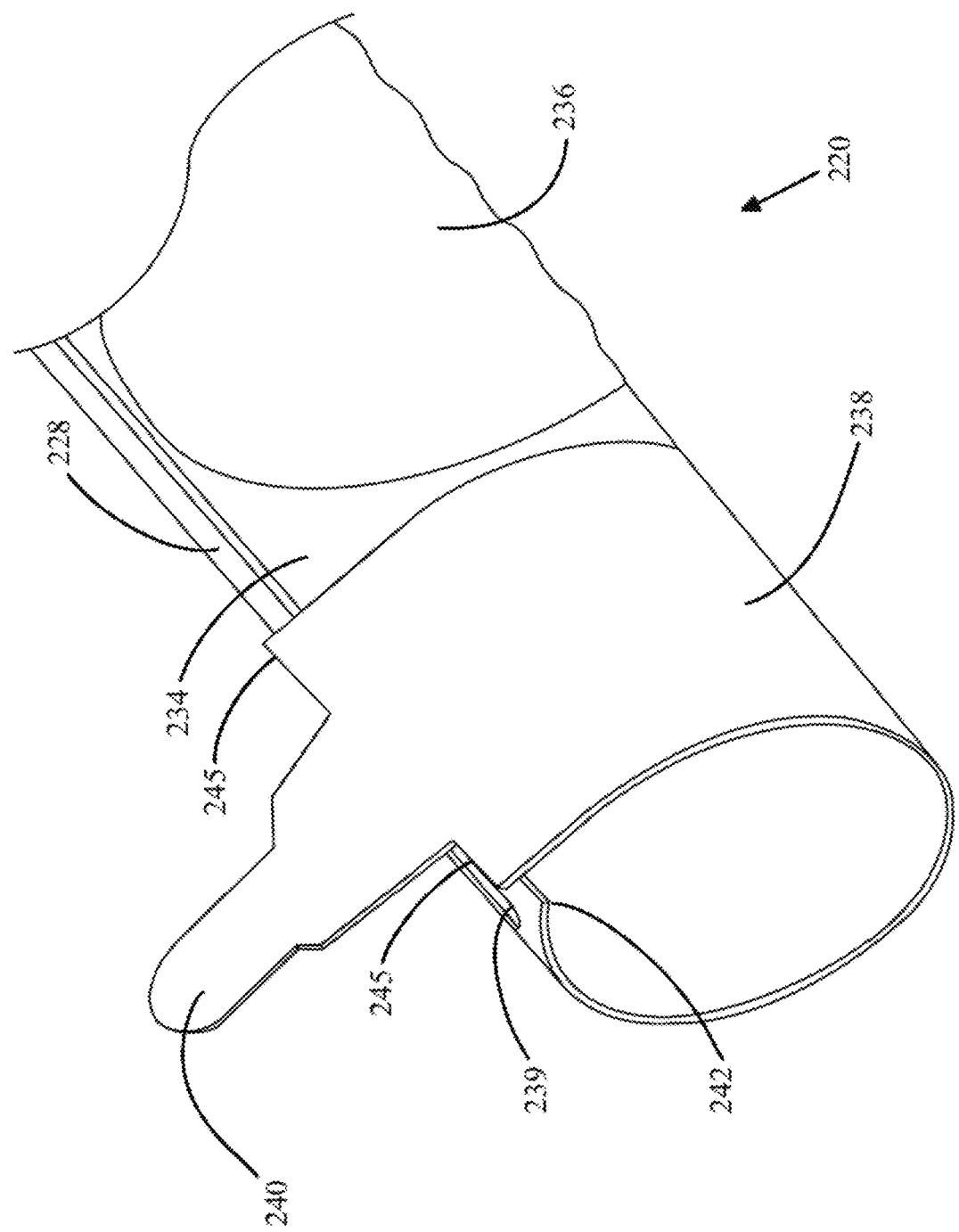
FIGS. 5A and 5B illustrates an endoscopic accessory device joined into a tubular structure prior to securing the tip of an endoscope.
Figure 5B:
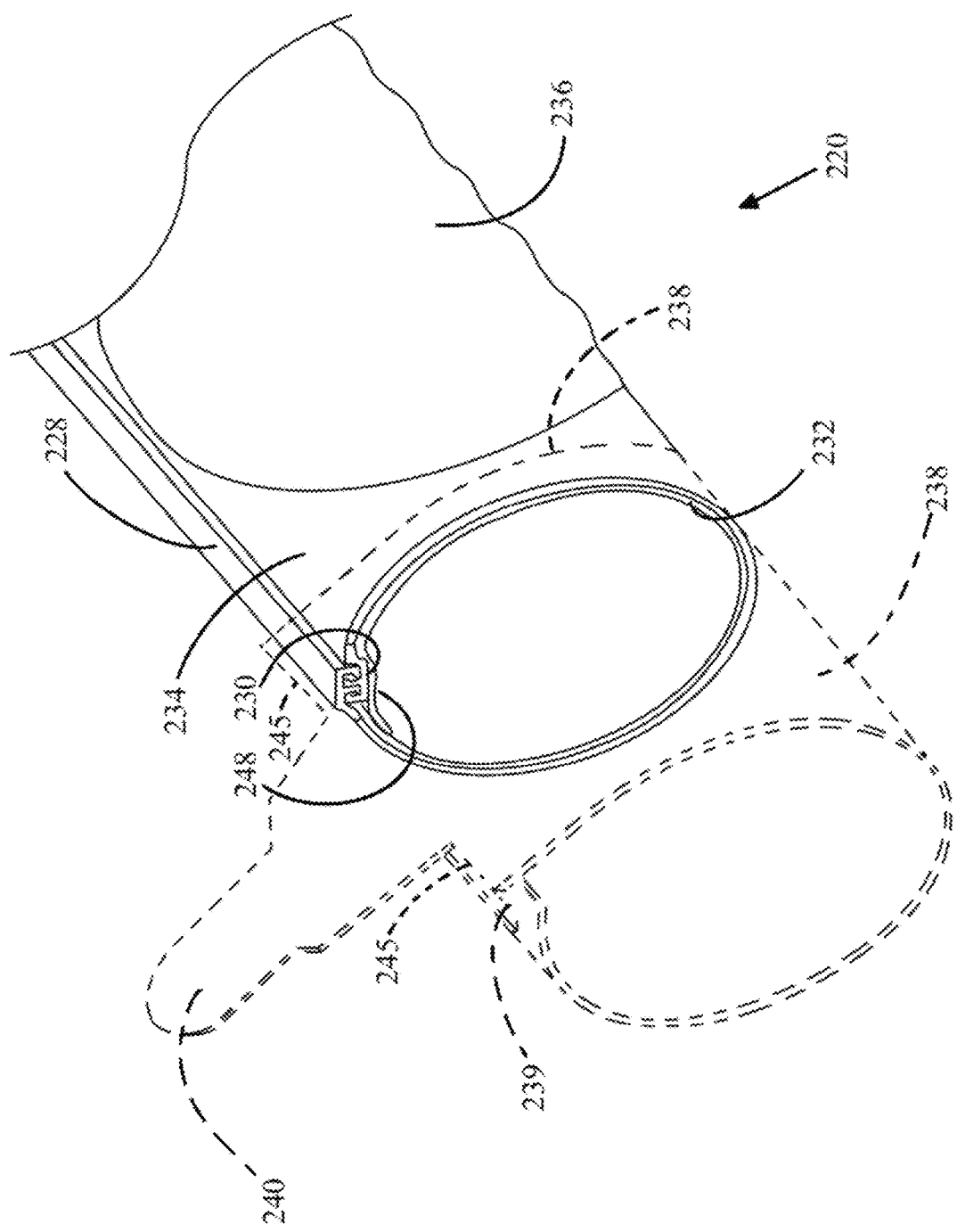

FIGS. 5A and 5B illustrates an endoscopic accessory device 220 joined into a tubular structure but prior to securing the tip 238 about an endoscope. FIG. 5A illustrates a belt 240 of the tip 238 as wrapping towards the opening slit 239. As noted herein, a distance from the shoulder 241 of the tip 238 to a position of the opening 239 limits the diameter of the tip 238 to prevent the distal opening to be too large or over-tightening on an endoscope, while the adhesive regions 241 allows for maintaining the tip 238 in a closed configuration. In variations shown in FIGS. 5A and 5B, the proximal edge 235 of the tip 238 overlaps the seam structure 228/230. In both FIGS. 5A and 5B the exterior balloon 236 is shown in an uninflated state. However, in FIG. 5B the tip 238 is transparent to illustrate the seam structures 228 230 as joined together. In addition, the inner flap 248 overlaps the seam structures 228 230 to assist in reducing friction of the endoscope over the seam and creating a fluid seal at the seam. For purposes of illustration, the Figures show the inner layer 232 and outer layer 234 as directly adjacent to each other. However, as noted above, the layers 232 234 can be spaced to accommodate lumens, passages, and/or tubing of filled with fluid as discussed above.

Figure 5C:
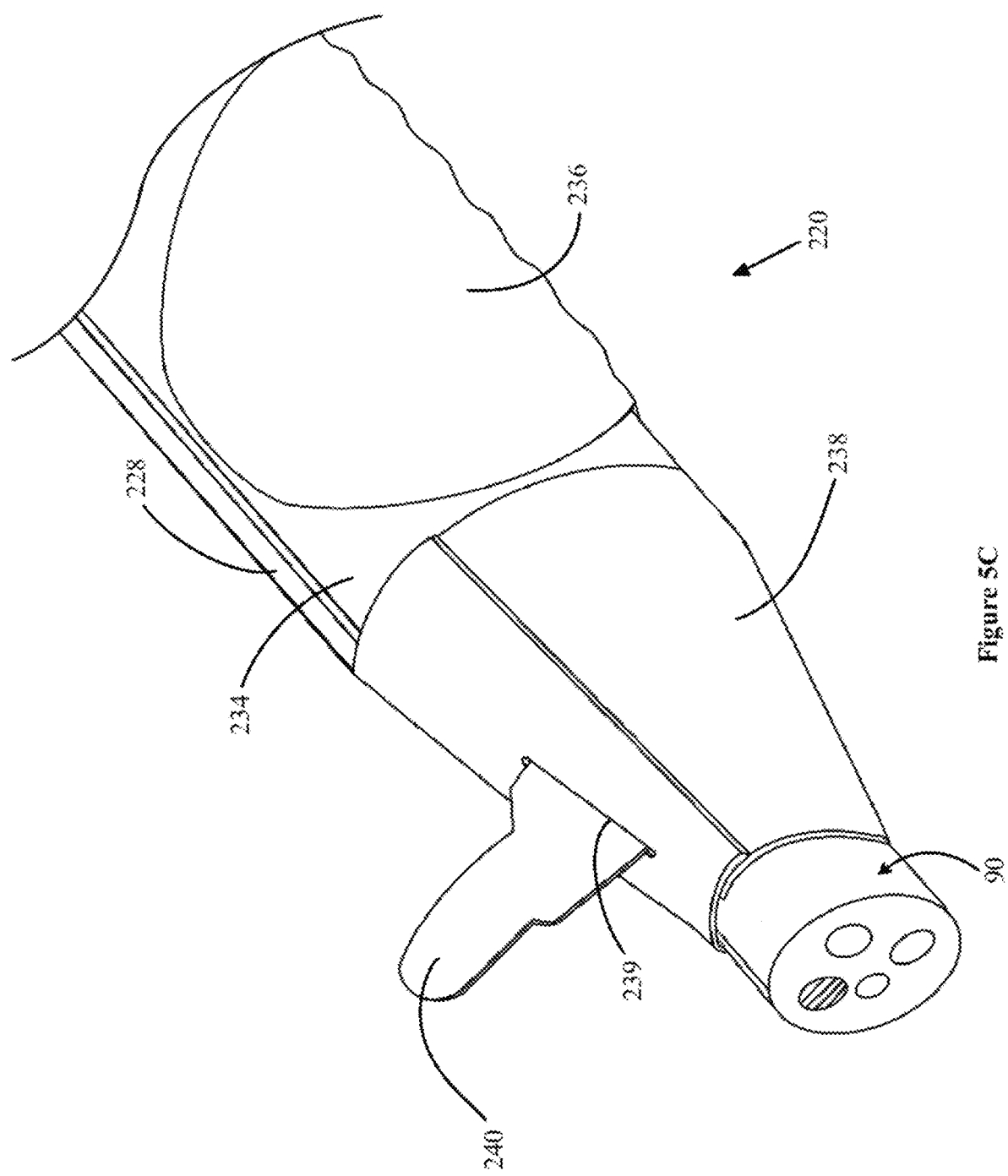
FIG. 5C shows a state where an end of the tip material is inserted through the opening and prior to being secured to the remainder of the tip material.

FIG. 5C shows a state where a belt 240 of the tip 238 is inserted through the opening slit 239 and the adhesive removeable cover is removed from the adhesive region to secure the overlapping region of the tip 238. The belt 240 of the tip 238 is then wrapped around and can be secured to the tip 238 as shown in FIG. 1.

Figure 6A:
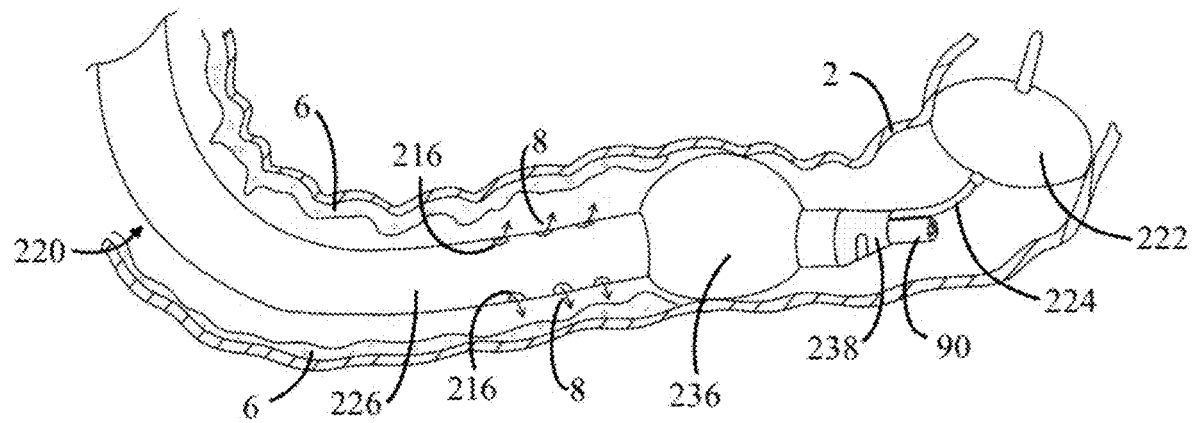
FIGS. 6A and 6B illustrate a variation of an endoscopic accessory device when positioned within a colon where the device can clean or prepare the colon for examination.
Figure 6B:
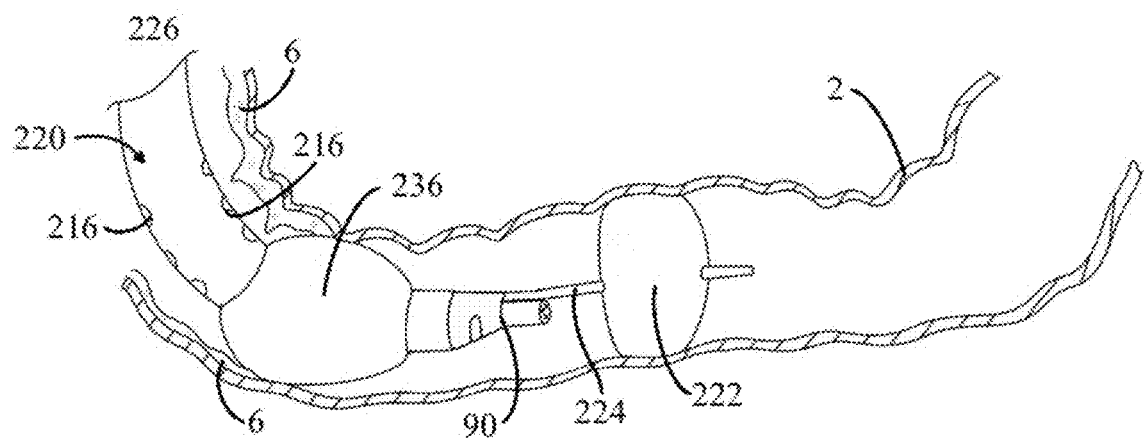

FIGS. 6A and 6B illustrate a variation of an endoscopic accessory device 220 when positioned within a colon 2. As shown, a catheter balloon 224 and endoscope 90 extend from a tip 238 of the device 220. When the distal balloon 222 of the catheter 224 is expanded, the region between the proximal balloon 236 and the distal balloon 222 on the catheter balloon 224 establishes an endoluminal compartment for improved examination of the colon 2 (or other body region) for examination of polyps and adenoma detection. However, the device 220 can also be used in situations where the colon is insufficiently prepared (poor prep) or not prepared (no prep) for a colonoscopy such that waste 6 remains in the colon 2.

FIG. 6A illustrates the device 220 in a configuration where the proximal balloon 236 is inflated and fluid is delivered into the colon 2. The device 220 can optionally include fluid ports 216 that deliver fluids at low or high pressure to aid in cleaning the colon 2. Alternatively, or in combination, fluid can be delivered to the colon 2 not using the accessory device 220. FIG. 6A also shows the distal balloon 222 of the catheter balloon 224 expanded. Optional variations include cleaning of the colon 2 without inflating the balloon 222 on the catheter 224. Moreover, additional variations can include a device 220 where some ports 216 are used as vacuum ports to remove fluid.

FIG. 6B illustrates movement of the accessory device 220 and inflated balloons 236 in a rearward direction such that the balloons 236 perform a squeegee function to propel both fluid and fecal matter 6 away from the region to be examined (i.e., the region between balloons 222 236) while wiping the intestinal wall of fluid secretion and other residual matter.

FIGS. 7A to 7G illustrate another variation of an endoscopic accessory device 220 for performing a right colonic enema.

Figure 7A:
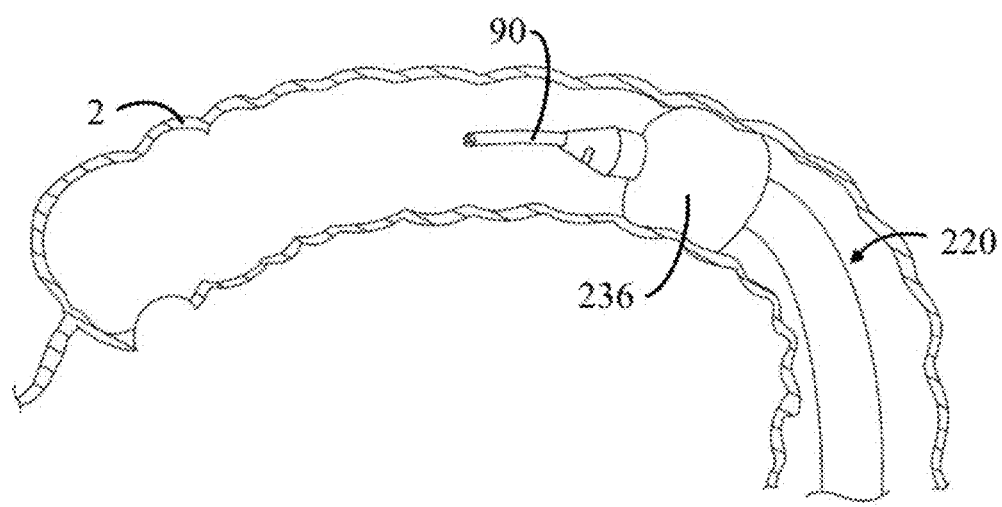
FIGS. 7A to 7G illustrate another variation of an endoscopic accessory device for performing a right colonic enema with a variation of an endoscopic accessory device.

FIG. 7A illustrates the right colon 2 where an endoscope 90 can be positioned without the accessory device 220. Once positioned the accessory device 220 can be fastened about the endoscope 90 and advanced into position. Once in position the proximal balloon 236 is expanded.

Figure 7B:
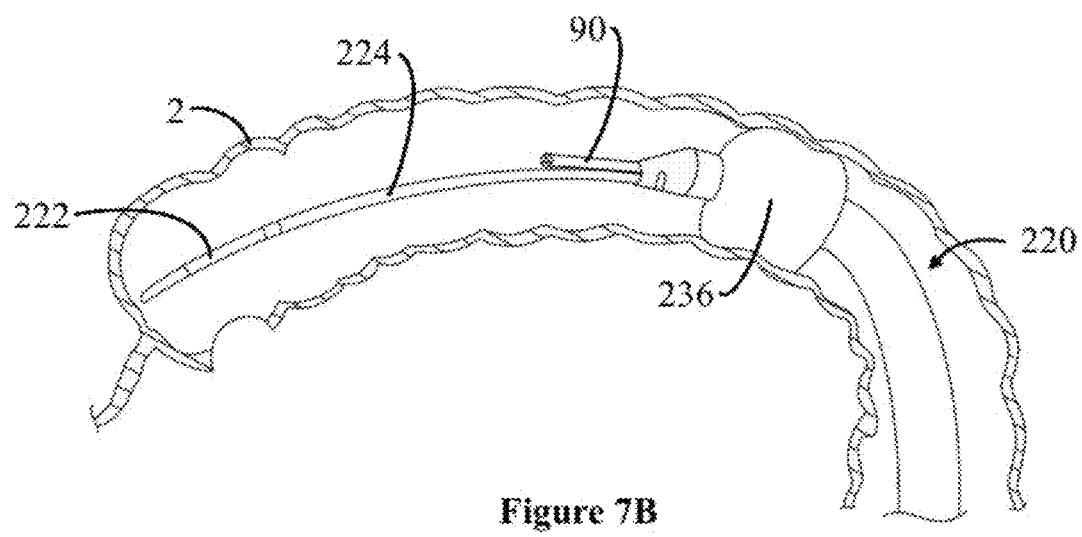
Figure 7C:
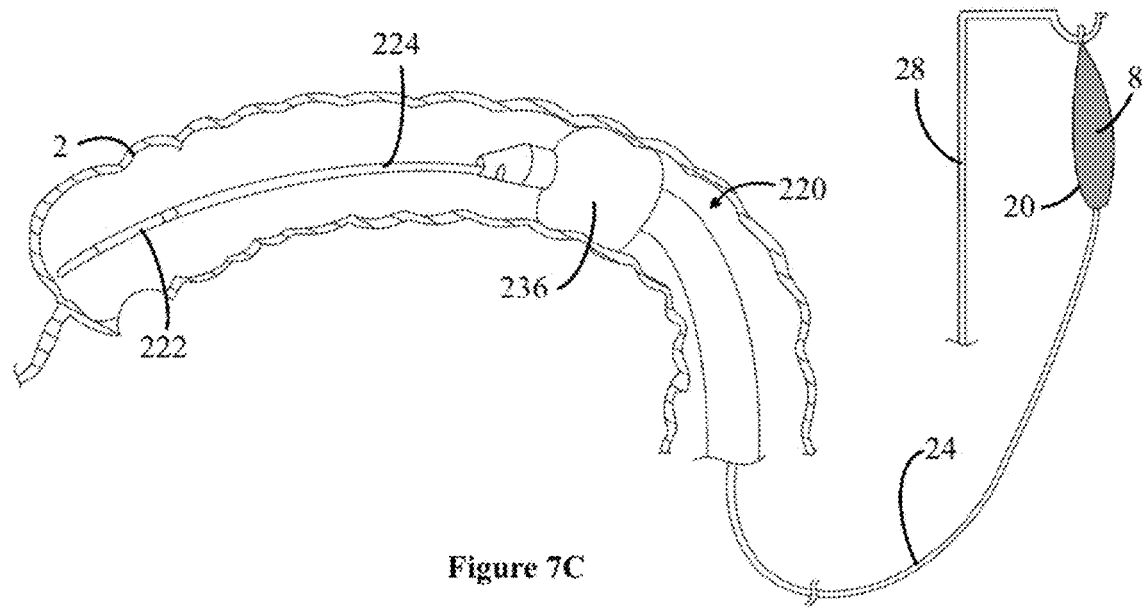
Figure 7D:
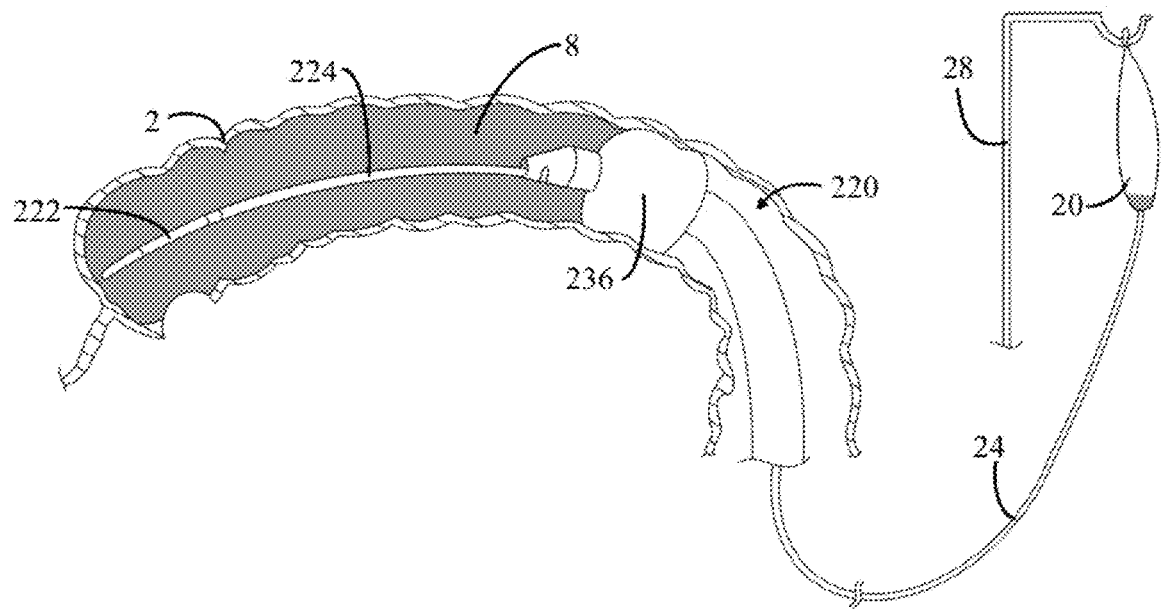

FIG. 7B illustrates the accessory device 220 and endoscope 90 remaining in position as a balloon catheter 224 is advanced distally to the device 220. FIG. 7C shows optional removal of the endoscope from the device 220. The device can be coupled to a fluid source such as a bag 20 containing a fluid 8. The bag 20 is coupled to a hub (not shown) of the accessory device 220 via a fluid line 24. FIG. 7c illustrates the bag 20 in an elevated position such that, as shown in FIG. 7D, gravity causes the fluid 8 to pass through the accessory device 220 and into the right colon 2.

Figure 7E:
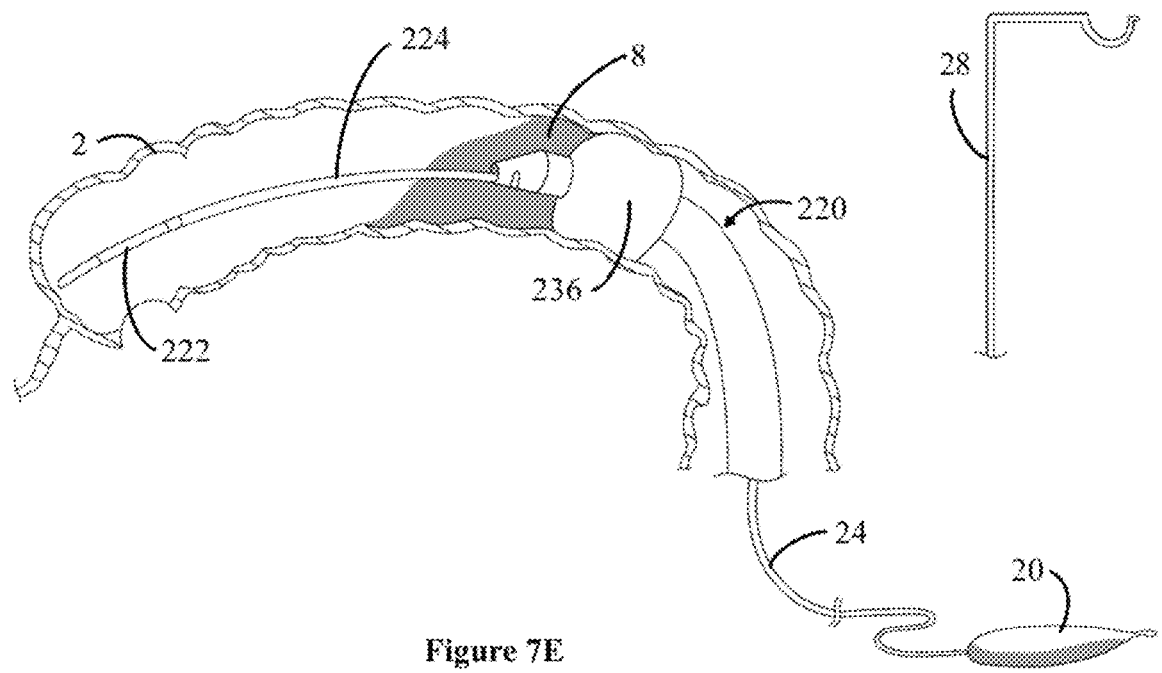

Next, after the fluid 8 is within the colon 2 for a sufficient time, the bag can then be placed lower than the patient, as shown in FIG. 7E so that gravity causes the fluid and waste to flow back into the same bag 20. It is noted that the balloon 222 of the balloon catheter 224 can remain inflated or uninflated.

Figure 7F:
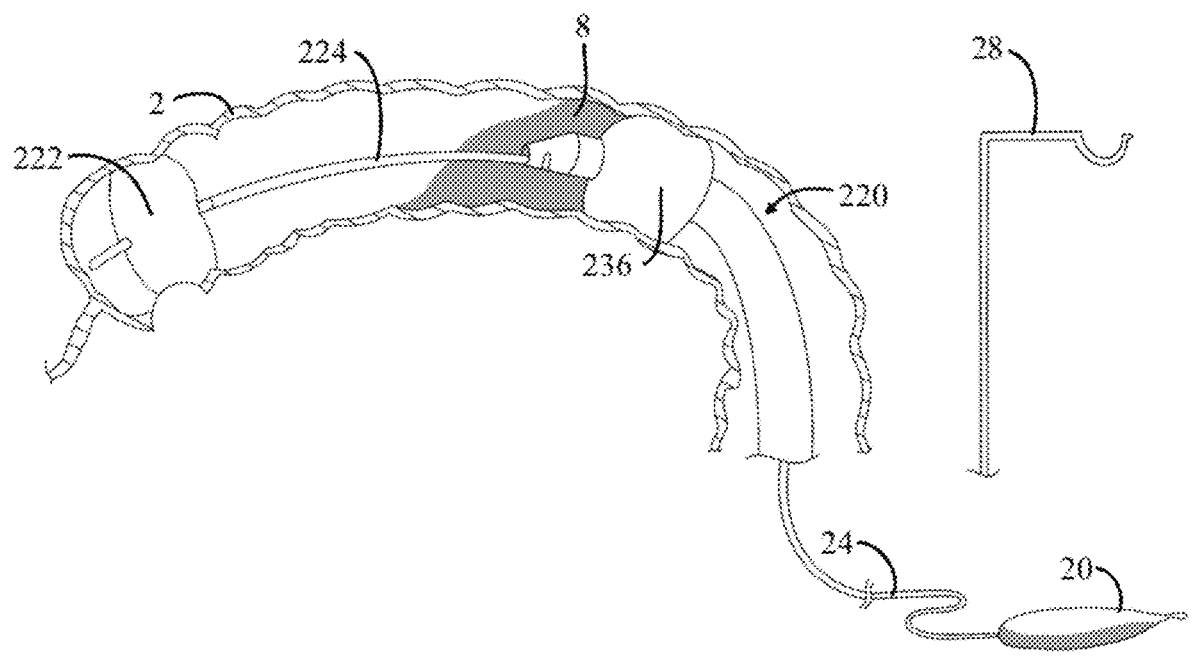
Figure 7G:
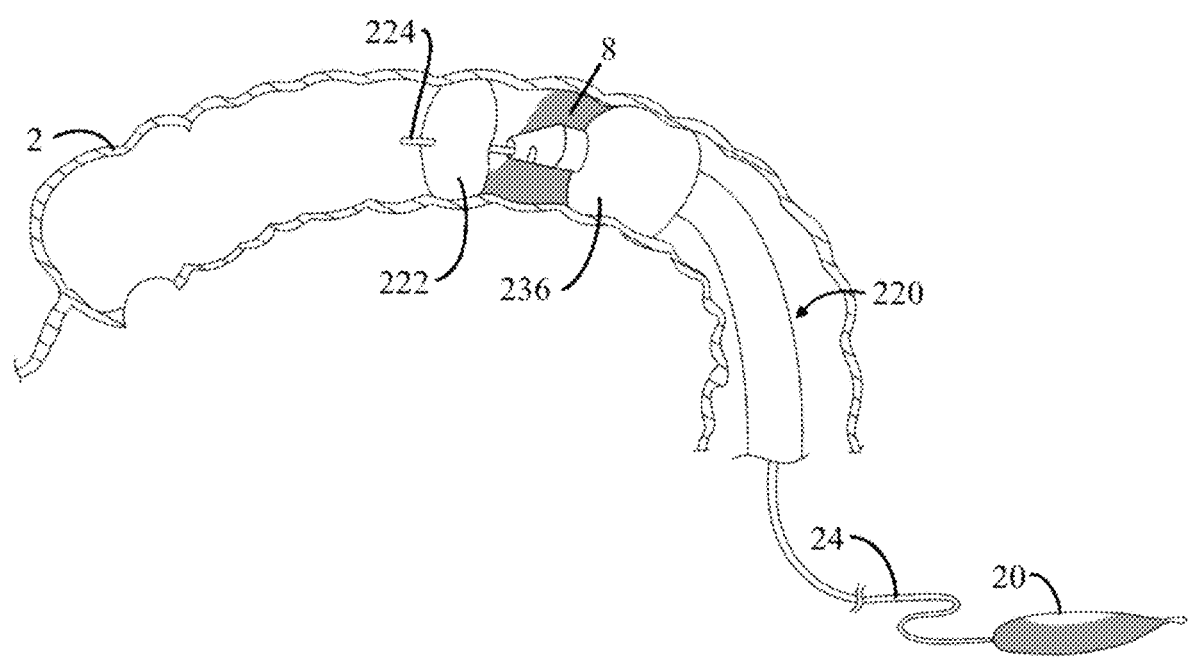

As an alternative variation and as shown in FIG. 7F, once the fluid drains by the force of gravity, the balloon 222 can be inflated and the balloon catheter 224 is pulled backward inside the colon 2 and retracted within the device 220 to clear residual fluid 8 from the colon. It is noted that the device 220 can remain in place. FIG. 7G illustrates the balloon 222 and catheter 224 pulled towards the device 220 such that additional fluid 8 is driven into the device 220 and into the bag 20 via the line 24. The line 24 can then be disconnected from the device 220, and the bag 20 with the line 24 can then be discarded. The endoscope 9 can then be reintroduced into the device 220 to the colon 2 inside the endoluminal compartment (not shown).

Figure 8A:
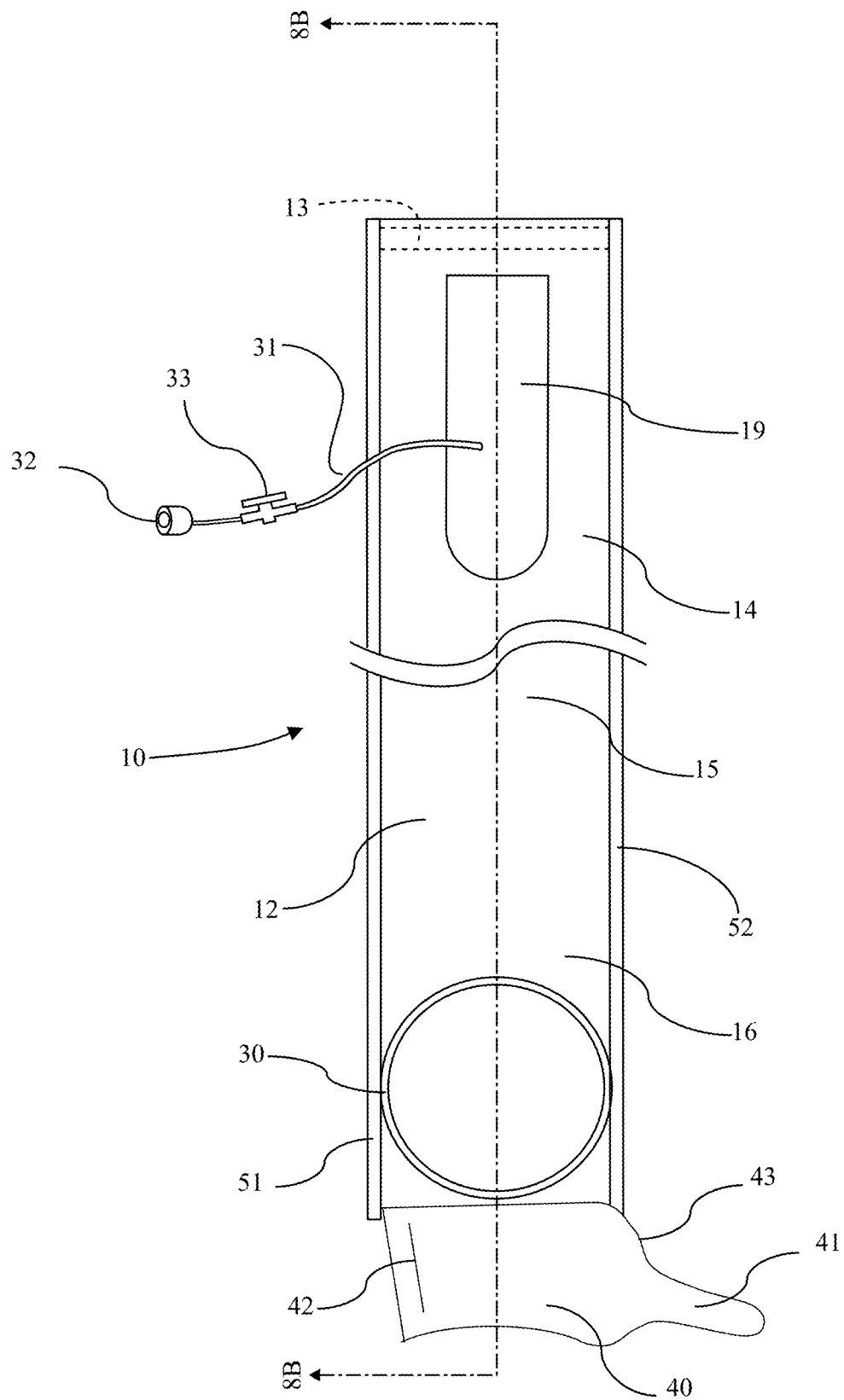
FIG. 8A illustrates another variation of an accessory device.

FIG. 8A illustrates another variation of a device 10 similar to the devices described above in that the accessory device 10 can define a cylindrical central through passageway for receiving an endoscope shaft for positioning into a body cavity such as gastrointestinal tract. The view is taken from an exterior of the device 10 showing an exterior surface 12.

Accessory device 10 can be composed of two flexible sheets, internal 110 and external 210, that are welded over each along the length of the accessory device 10. As noted above, the construction of the accessory device 10 can comprise a single sheet/structure or more than two sheets The accessory device has an external surface 12 and an internal surface (not shown in FIG. 8A), a proximal portion 14, a midportion 15, a distal end portion 16. When closed into a tubular shape, the accessory device 10 can include a proximal opening and a distal opening. Accessory device 10 can optionally include one or more hubs 19 for manipulating the device outside of the body. In such cases, the hub 19 can be located at the proximal end portion 14. The hub 19 can be used for manipulation of the accessory device 10 within the body cavity from an exterior of the body cavity. Hub 19 can also be used for connection of various inflation tubes. It is noted that the hub 19 can be low profile or even optional. In such a case, an inflation tube 31 can be directly coupled to an exterior expandable member 30. The inflation tube 31 can include any number of fittings and/or attachments such as a luer lock 32 and a valve 33.

As noted above, the accessory device 10 can include a longitudinal seam 50 along its entire length that allows opening of accessory device 10 along its entire length for placing an endoscope shaft within accessory device 10 that is already positioned within the body without removing the endoscope shaft from the body cavity.

FIG. 8A also illustrates the device 10 having a raised barrier (relative to an inner surface of the device 10) or block 13 such as a foam cuff on an inner surface at the proximal end portion 14 of the accessory device 10. In additional variations, the block 13 can be multiple components and made from one or more elastomeric substances and be located at any point along the length of accessory device 10. In use, the block 13 forms a fluid barrier when the accessory device is formed into a tubular structure over an endoscope or over a fluid tube used for irrigation as described below.

FIG. 8A also shows the device 10 as having at least one inflatable proximal balloon 30 located on an outer surface 12 at the distal end portion 16 of the accessory device 10. The inflation tube 31 can be configured to supply fluid to the proximal balloon 30 and can runs along the accessory device 10 either between the sheets or within an interior/exterior of the device. The inflation tube 31 can terminate in a luer lock 32 after exiting hub 19 at the proximal end portion 14 of accessory device 10.

As discussed above, the accessory device 10 can include edge portions 51 and 52 that join to form a seam to configure the accessory device 10 in a tubular configuration. FIG. 8A also shows a distal tip 40, as described above, that includes a belt 41 that passes through an opening 42 and is pulled through until it reaches the shoulder 43 of the belt 41, which provides a hard stop to control an interior diameter of the closed tip 40. Assembly of the tip 40 allows for closure over an endoscope.

Figure 8B:
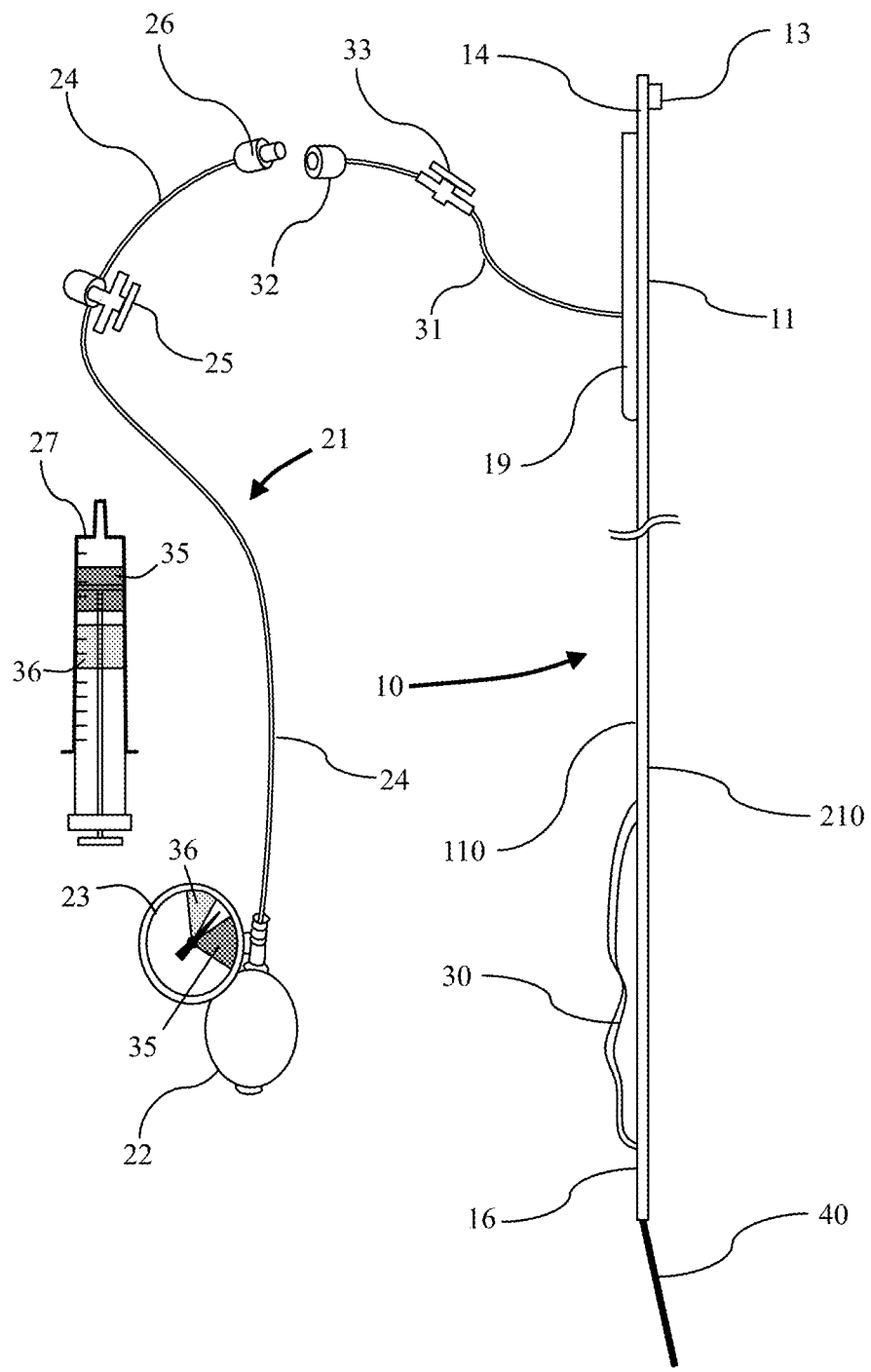
FIG. 8B shows various examples of inflations sources for expanding an exterior balloon of the device.

FIG. 8B, which is a sectional view of the accessory device 10 taken along line 8B-8B of FIG. 8A shows various examples of inflation sources 21 for expanding an exterior balloon 30. For example, a syringe 27 and/or a pump 22 can be used as inflation sources. Again, any number of components can be used with the inflation devices 21. For example, FIG. 8B shows the pump 22 including a gauge 23, tubing 24, connector 26 and optional valve 25. The inflation devices 21 can be coupled to the accessory device 10 for inflation of the distal balloon 30. FIG. 8B also illustrates a block 13 on an interior surface 210 of the device 10 at the proximal end portion 14. In the variation of the accessory device 10 shown in FIGS. 8A and 8B, there is only one or more exterior balloons 30. As described below, the balloon 30 can provide anchoring as well as a cleaning function depending on the expansion or pressure of the balloon 30 against the body passageway. Accordingly, the pressurization or inflation sources 21 can include indicators 35, 36 that allow the user to determine the state of the balloon 30. The marking 35 indicating a higher pressure can be correlated to the balloon 30 being in an anchoring state and the marking 36 indicating a lower pressure 36 can correlate to a balloon 30 in an expanded state but where the balloon 30 can be translated within the body passage to perform a cleaning function.

Figure 8C:
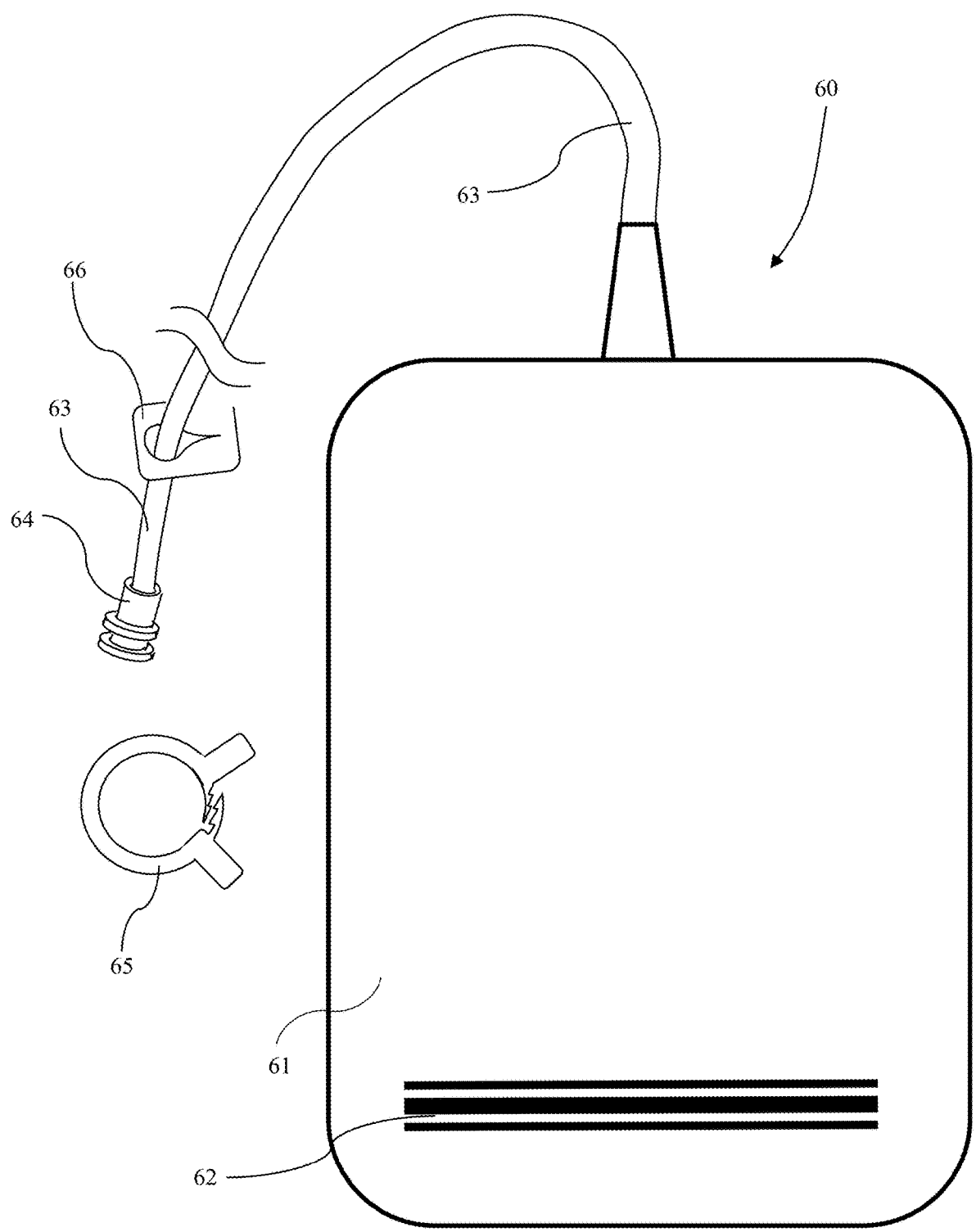
FIG. 8C shows an irrigation/drainage kit for use with accessory devices described herein.

FIG. 8C shows an irrigation/drainage kit 60 for use with the accessory devices includes a fluid bag 61 with resealable opening 62 connected to a fluid bag tube 63 having a connector 64 and a tube clamp 65. The kit 60 can optionally include a slit valve 66 that controls of passage of fluid through fluid tube 63. The kit 60 can include an optional clamp 65 to secure the accessory device 10 to the connector 64.

Figure 8D:
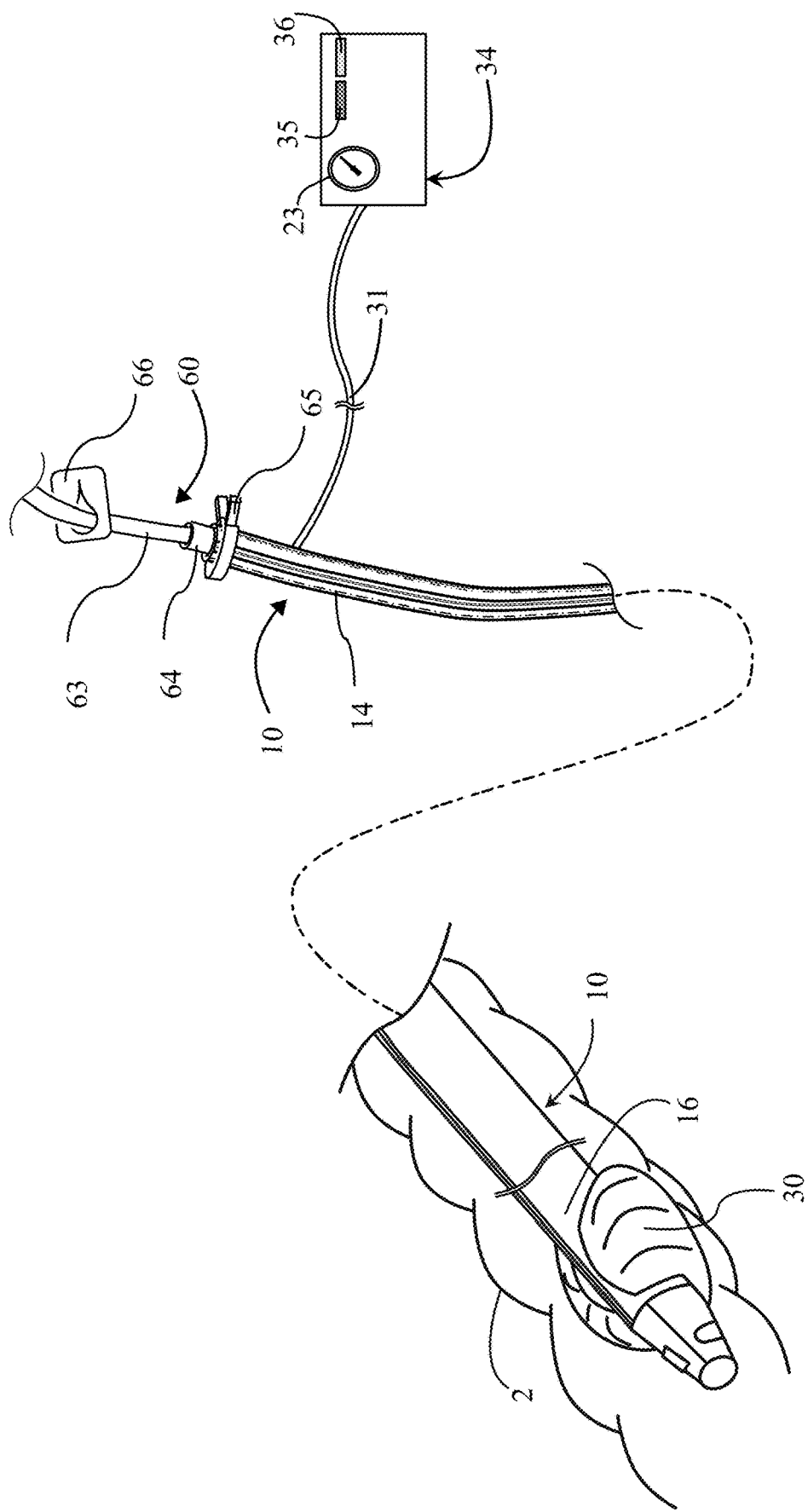
FIG. 8D illustrates an accessory device as discussed in FIGS. 8A and 8B with an irrigation/drainage kit connected to the device.

FIG. 8D illustrates an accessory device 10 as discussed in FIGS. 8A and 8B with an irrigation/drainage kit 60 connected to the device 10 (the bag is not illustrated in FIG. 8D). In practice, the device 10 is initially positioned over a colonoscope or endoscope (not shown) and is then advanced to the target area, in this case the right colon. The balloon 30 is then inflated to anchor the device 10 and prevent leakage of fluid around the balloon 30.

As shown, a connection piece 64 is inserted into the accessory device 10 in lieu of the endoscope. The connection piece is placed against the block or cuff (not shown) and can be secured with a clamp 65. Fluids can be infused within the body cavity/colon 2 via the lumen of accessory device 10. The flow of fluid within the irrigation tube 63 can be controlled using a valve 66. Wastewater can be drained from the colon 2 via the lumen of accessory device 10 and the exterior balloon 30 at the distal portion 16 of the accessory device 10 can be expanded and withdrawn against the lumen wall to provide additional cleaning of the body passage.

As shown in FIG. 8D, the accessory device 10 can be advanced into the body cavity/colon 2 to reach an end of an endoscope (not shown) previously positioned therein. Optionally, the device 10 can be advanced over the tip of the endoscope so that the device 10 is viewable under endoscopic examination. Next, the accessory device 10 can be withdrawn to ensure that a distal end 16 of the accessory device 10 is situated just proximal to the endoscope tip 91. Next, the proximal balloon 30 can be inflated to secure the position of accessory device 10 within the body cavity 2. Optionally, expansion of the balloon 30 can create a seal between against a wall of the body cavity 2.

Next, the endoscope can be withdrawn from the accessory device 10 and the body cavity 2 so that the accessory device 10 is connected to the irrigation/drainage kit 60 shown in FIG. 8D. Next, the body cavity 2 can be lavaged as described above. In addition, the accessory device 10 can be withdrawn from the body cavity 2 with the proximal balloon 30 causing a squeegee effect against the walls of the body cavity. This cleaning can provide improving the view of the cavity by the endoscope during colonoscopy to increase adenoma detection rate. As noted herein, the balloon 30 can serve an anchoring function as well as a cleaning function depending on the pressure/expansion of the balloon 30 against the body passageway. FIG. 8D illustrates an automated system 34 that can deliver fluid to the balloon 30 using an inflation tube 31 coupled to the system 34. The system 34 can include a pressure gauge 23 and provide indicators 35, 36 to inform the user of whether the balloon 30 is in an anchored state 35 or in the lower pressure state that allows for a cleaning configuration 36.

After completion of the examination, the balloon 30 can be deflated to permit removal of the accessory device 10 as well as endoscope. It is noted that either device can be removed independently of each other from the body cavity.

The use of the device shown in FIGS. 8A to 8D to clean a body cavity, is similar to that described above, with the exception being the accessory device in FIGS. 8A to 8D can directly couple to a tubing of the irrigation/drainage kit without a hub on the accessory device 10. Moreover, this variation of the accessory device 10 can optionally include or omit a distal balloon and/or an interior balloon as discussed above with alternate variations of the accessory device.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

The scope of the present invention, therefore, is not intended to be limited to the exemplary aspects shown and described herein. Rather, the scope and spirit of present invention is embodied by the appended claims.

I claim:

1. A method of preparing a colon for examination having an endoscope positioned within the colon, the method comprising:

advancing an endoscopic accessory device over the endoscope, the endoscopic accessory device including a first balloon adjacent to a distal opening;

expanding the first balloon against a wall of the colon;

removing the endoscope from the endoscopic accessory device and securing a proximal end of the endoscopic accessory device directly to a tubing of a fluid reservoir having a fluid such that the proximal end of the endoscopic accessory device forms a seal against the tubing;

delivering the fluid through the endoscopic accessory device to the colon by positioning the fluid reservoir above the endoscopic accessory device such that gravity causes the fluid to flow into the colon through the tubing and through the endoscopic accessory device;

draining the fluid from the colon by lowering the fluid reservoir below the endoscopic accessory device such that gravity causes a portion of the fluid to drain into the fluid reservoir; and withdrawing the first balloon from a portion of the colon while the first balloon is expanded to further prepare the colon for examination.

2. The method of claim 1, where expanding the first balloon against the wall of the colon comprises expanding the first balloon to a first pressure such that the first balloon anchors the endoscopic accessory device within the colon.

3. The method of claim 2, further comprising providing an indicator to notify an operator that the endoscopic accessory device is anchored within the colon.

4. The method of claim 1, further comprising reducing a pressure of the first balloon prior to withdrawing the first balloon, where the first balloon remains expanded against the wall of the colon.

5. The method of claim 4, further comprising providing an indicator to notify an operator that the endoscopic accessory device is in a cleaning configuration.

6. An accessory device, for use with an endoscope or a tubular structure of an irrigation kit, the endoscopic accessory device comprising:
- a wall structure having a proximal portion spaced in a lengthwise direction from a distal portion along an axis, the wall structure having a first edge and a second edge extending parallel to the axis in the lengthwise direction from a proximal end of the proximal portion to a distal end of the distal portion and separated by a wall structure width, wherein the wall structure includes an interior surface, an exterior surface, and an intermediate space therebetween;
- a tip material located at the distal portion and having a tip length extending distally beyond the distal end, the tip material having a tip width greater than the wall structure width;
- a first seam structure extending along the first edge and a second seam structure extending along the second edge; and
- a proximal balloon located on the exterior surface at the distal portion;
- a raised barrier located at the proximal portion; and
- wherein in a pre-deployment configuration the proximal balloon is uninflated, and the wall structure is sufficiently flexible to assume a flat profile across the wall structure width;
- wherein the first seam structure can be releasably joined to the second seam structure to form a fluid tight seal therebetween such that the wall structure can form a closed overtube profile about the endoscope;
- a clamp configured for coupling to the wall structure when in the closed overtube profile;
- wherein in the closed overtube profile the tip width of the tip material permits the tip material to circumferentially overlap the distal end and where the raised barrier forms a fluid barrier when the clamp is engaged over the wall structure and the tubular structure of the irrigation kit without the use of a hub on the wall structure.

7. The accessory device of claim 6, where the interior surface includes a flange portion extending over the first seam structure such that in the closed overtube profile the flange portion covers the first seam structure and the second seam structure when joined together.

8. The accessory device of claim 6, where a flexibility of the distal portion is greater than a flexibility of the proximal portion.

9. The accessory device of claim 8, where a material of the tip material is different from a material of the distal portion.

10. The accessory device of claim 6, further comprising at least one adhesive region on the tip material, such that the at least one adhesive region permits securing a first portion of the tip material to a second portion of the tip material in a conical or tubular shape.

11. The accessory device of claim 6, wherein the tip material comprises a slit and a stop surface, such that when an end of the tip material is inserted into the slit, the tip material forms a conical or tubular shape, wherein the stop surface limits advancement of the end of the tip material into the slit to limit an inner diameter of the tip material.

12. The accessory device of claim 6, wherein when in the closed overtube profile a portion of the tip material overlaps a portion of the first seam structure and the second seam structure.

13. The accessory device of claim 6, wherein the first seam structure comprises a first alignment surface adjacent to the tip material, and where the second seam structure comprises a second alignment surface adjacent to the tip material, wherein the first alignment surface nests with the second alignment surface to align the first seam structure to the second seam structure.

14. The accessory device of claim 6, wherein when in the closed overtube profile the tip material is configured to form a conical shape at an end of the closed overtube profile.

15. The accessory device of claim 6, further comprising a hydrophilic or a hydrophobic coating on the interior surface and/or the exterior surface of the wall structure.

16. The accessory device of claim 6, further comprising an inflation source having at least a first indicator and a second indicator, wherein, when coupled to the proximal balloon, the first indicator denotes a pressure of the balloon in an anchoring configuration when positioned within a patient, and where the second indicator denotes the pressure of the balloon in a cleaning configuration.

17. The accessory device of claim 16, wherein the inflation source comprises a pump having a gauge, where the first indicator and the second indicator are on the gauge.

18. The accessory device of claim 16, wherein the inflation source comprises a syringe and where the first indicator and the second indicator are on the syringe.

19. The accessory device of claim 16, wherein the inflation source comprises an automated system configured to deliver fluid to the proximal balloon, where the first indicator and the second indicator are located on the automated system.

* * * * *